(12) United States Patent
Wolf et al.

(10) Patent No.: US 7,700,822 B2
(45) Date of Patent: Apr. 20, 2010

(54) MODULATION OF CYTOCHROME P450 REDUCTASE ACTIVITY

(75) Inventors: Charles Roland Wolf, Dundee (GB); Colin J. Henderson, Dundee (GB)

(73) Assignee: Cancer Research Technology Limited, London (GB)

( * ) Notice: Subject to any disclaimer, the term of this patent is extended or adjusted under 35 U.S.C. 154(b) by 662 days.

(21) Appl. No.: 10/306,559

(22) Filed: Nov. 27, 2002

(65) Prior Publication Data

US 2004/0010809 A1 Jan. 15, 2004

Related U.S. Application Data

(60) Provisional application No. 60/410,057, filed on Sep. 12, 2002.

(30) Foreign Application Priority Data

Jul. 12, 2002 (GB) ................................. 0216203.0

(51) Int. Cl.
*G01N 33/00* (2006.01)
*A01K 67/027* (2006.01)
*A01K 67/00* (2006.01)

(52) U.S. Cl. .................................. 800/3; 800/18; 800/8
(58) Field of Classification Search .................... 800/3, 800/18, 8; 435/325
See application file for complete search history.

(56) References Cited

U.S. PATENT DOCUMENTS

| 5,767,337 A | 6/1998 | Roses et al. |
| 6,066,778 A | 5/2000 | Ginsburg et al. |
| 6,207,648 B1 | 3/2001 | Waxman et al. |
| 6,387,647 B1 | 5/2002 | Kirsch et al. |

FOREIGN PATENT DOCUMENTS

| EP | 1 206 906 A1 | 5/2002 |
| WO | WO 97/05247 | 2/1997 |
| WO | WO 00/14256 | 3/2000 |
| WO | WO 02/35923 | 5/2002 |
| WO | WO 02/36784 A1 | 5/2002 |

OTHER PUBLICATIONS

Henderson C J Sahraouei. A. and. Wolf C. R Cytochrome P450s and chemoprevention Biochemical Society Transactions. (2000), 28(2): 42-46.*
Postic C, Shiota M, Niswender KD, Jetton TL, Chen Y, Moates JM, et al., Dual roles for glucokinase in glucose homeostasis as determined by liver and pancreatic beta cell-specific gene knock-outs using Cre recombinase. J Biol Chem. 1999;274(1):305-15.*
Holschneider DP and Shih JC. Genotype to phenotype: challenges and opportunitiesInt.2000 J. Devl Neuroscience 18: 615-618.*
Taurog JD, Lowen L, Forman J, Hammer RE. HLA-B27 in inbred and non-inbred transgenic mice. Cell surface expression and recognition as an alloantigen in the absence of human beta 2-microglobulin. J Immunol. 1988 ;141(11):4020-3.*
Houdebine LM. Production of pharmaceutical proteins from transgenic animals. J Biotechnol. 1994;34(3):269-87.*
Mullins LJ, Mullins JJ. Transgenesis in the rat and larger mammals. J Clin Invest. 1996 ;97(7):1557-60.*
Campbell KHS and Wilmut I. Totipotency or multipotentiality of cultured cells:Applications and progress Theriogenology 1997, 47:63-72.*
Moreadith RW, Radford NB. Gene targeting in embryonic stem cells: the new physiology and metabolism. J Mol Med. 1997;75(3):208-16.*
Mullins JJ, Sigmund CD, Kane-Haas C, Gross KW, McGowan RA. Expression of the DBA/2J Ren-2 gene in the adrenal gland of transgenic mice. EMBO J. 1989;8(13):4065-72.*
Mullins JJ, Peters J, Ganten D. Fulminant hypertension in transgenic rats harboring the mouse Ren-2 gene.Nature. 1990;344(6266):541-4.*
Hammer RE, Maika SD, Richardson JA, Tang JP, Taurog JD. Spontaneous inflammatory disease in transgenic rats expressing HLA-B27 and human beta 2m: an animal model of HLA-B27-associated human disorders. Cell. 1990;63(5)1099-112.*
Tailleux A, Torpier G, Mezdour H, Fruchart JC, Staels B, Fievet C. Murine models to investigate pharmacological compounds acting as ligands of PPARs in dyslipidemia and atherosclerosis. Trends Pharmacol Sci. 2003;24(10):530-4.*
Cosgrove D, Rodgers K, Meehan D, Miller C, Bovard K et al. Integrin alpha1beta1 and transforming growth factor-beta1 play distinct roles in alport glomerular pathogenesis and serve as dual targets for metabolic therapy. Am J Pathol. 2000 ; 157(5):1649-59.*
Ryding AD, Sharp MG, Mullins JJ. Conditional transgenic technologies. J Endocrinol. 2001; 171(1):1-14.*
Gonzalez et al Toxicol. Letters, 2001; 120(1-3): 199-208.*
den Boer et al Arterioscler Thromb Vasc Biol. 2004, 24(4):1-6.*
Buters et al Drug Metabolism Reviews, 1999, 21, 437-447.*
Otto et al Mol Cell Biol 23: 6103-6116 , Sep. 2003.*
Wang et al Biochem J. Jun. 15, 2005;388(Pt 3):857-67.*
Finn et al J Pharmacol Exp Ther. Jul. 2007;322(1):40-7.*
Buters et al., *Cytochrome P450 CYP1B1 determines susceptibility to 7,12-dimethylbenz[a]anthracene-induced lymphomas*, Proc. Natl. Acad. Sci. USA, vol. 96, Mar. 1999, pp. 1977-1982.

(Continued)

*Primary Examiner*—Deborah Crouch
*Assistant Examiner*—Anoop Singh
(74) *Attorney, Agent, or Firm*—Myers, Bigel, Sibley & Sajovec, P.A.

(57) ABSTRACT

The present invention relates to non-human transgenic animals, tissues and/or cells derived therefrom having depleted or ablated cytochrome P450 reductase (CPR) expression, methods of producing such animals, tissues and/or cells, and methods of using such animals, tissues and/or cells. Non-human transgenic animals, tissues and or cells derived therefrom of the present invention may be used for, but non exclusively, in both in vivo and in vitro screening of therapeutic agents, drug development, drug metabolism/disposition studies and studying disease states, pregnancy, fetal development, modulation of hormone function and hormone levels, and other pathways and/or substrate metabolism in which cytochrome P450 plays a role.

11 Claims, 5 Drawing Sheets

OTHER PUBLICATIONS

Dalton et al., *Targeted Knockout of Cyp1a1 Gene Does Not Alter Hepatic Constitutive Expression of Other Genes in the Mouse [Ah] Battery*, Biochemical and Biophysical Research Communications, vol. 267, 2000, pp. 184-189.

Deeni et al., *Expression, Purification, and Biochemical Characterization of a Human Cytochrome P450 CYP2D6-NADPH Cytochrome P450 Reductase Fusion Protein*, Archives of Biochemistry and Biophysics, vol. 396, No. 1, Dec. 1, 2001, pp. 16-24.

Imaoka et al., *A Transgenic Mouse Expressing Human CYP4B1*, Biochemical and Biophysical Research Communications, vol. 284, 2001, pp. 757-762.

Lee et al., *Role of CYP2E1 in the Hepatotoxicity of Acetaminophen*, The Journal of Biological Chemistry, vol. 271, No. 20, May 17, 1996, pp. 12063-12067.

Parikh et al., *Expression, Purification, and Characterization of a Catalytically Active Human Cytochrome P450 1A2:Rat NADPH-Cytochrome P450 Reductase Fusion Protein*, Protein Expression and Purification, vol. 9, 1997, pp. 346-354.

Pineau et al., *Neonatal lethality associated with respiratory distress in mice lacking cytochrome P450 1A2*, Proc. Natl. Acad. Sci. USA, vol. 92, May 1995, pp. 5134-5138.

Search Report under Section 17(5), Application No. GB 0316001.7, Nov. 25, 2003.

Search Report under Section 17(6), Application No. GB 0316001.7, Apr. 26, 2004.

International Search Report, PCT/GB03/02967, Jan. 5, 2004.

Ding et al., *A Mouse Model With Liver-Specific Deletion of the NADPH-Cytochrome P450 Reductase Gene*, Toxicological Sciences, vol. 71, No. S-1, Mar. 2003, p. 337.

Henderson et al., *Inactivation of the Hepatic Cytochrome P450 System by Conditional Deletion of Hepatic Cytochrome P450 Reductase*, The Journal of Biological Chemistry, vol. 279, No. 15, Apr. 11, 2003, pp. 13480-13486.

Wu et al., *Conditional Knockout of the Mouse NADPH-Cytochrome P450 Reductase Gene*, Genesis, vol. 36, Jul. 31, 2003, pp. 177-181.

Gu et al., *Liver-Specific Deletion of the NADPH-Cytochrome P450 Reductase Gene*, The Journal of Biological Chemistry, vol. 278, No. 28, Jul. 11, 2003, pp. 25895-25901.

Shen et al., *Association of Multiple Developmental Defects and Embryonic Lethality With Loss of Microsomal NADPH-Cytochrome P450 Oxidoreductase*, The Journal of Biological Chemistry, vol. 277, No. 8, Feb. 22, 2002, pp. 6536-6541.

International Preliminary Examination Report, PCT/GB 03/02967, Sep. 20, 2004.

Shen, Anna L., et al., Associatinof Multiple Developmental Defects and embryonic Lethality with Loss of Microsomal NADPH-Cytochrome P450 Oxidoreductase, *The Journal of Biological Chemistry*, vol. 277, No. 8, pp. 6536-6541 (Feb. 22, 2002).

Search Report under Section 17 for British Application Serial No. GB 0216203.0, Date of Search Mar. 25, 2003.

Human SOD1 Transgenic Strains from the Induced Mutant Resource, *JAX Notes; JAX® Mice Library* http://jaxmice.jax.org/html/jaxnotes/jaxn469c.shtml , #469 (Spring 1997).

Data Sheet, Transgenic mouse model, *M&B animal Models*, http://www.m-b.dk/Dataseets/C57-apoe.htm (2001).

Phenotypic Alleles, *Mouse Genome Informatics*, http://www.informatics.jax.org/searches/allele.cgi?456 (Nov. 22, 2002).

v-Ha-ras(TG.AC) OncoMouse™, *Taconic Animal Models*, http://www.taconic.com/anmodels/tranvha.htm (1998).

Su, L.K., et al., Multiple intestinal neoplasia casued by a mutation in the murine homolog of the APC gene, *Science*, vol. 256, No. 5057, Abstract, pp. 668-670 (May 1, 1992).

Agrawal, Alka, Aging Telomerase-Deficient, P53 Heterozygous Mice Develop Epithelial Tumors, *Nature*, vol. 406, Abstract, pp, 573-574, 641-645 (Aug. 10, 2000).

* cited by examiner

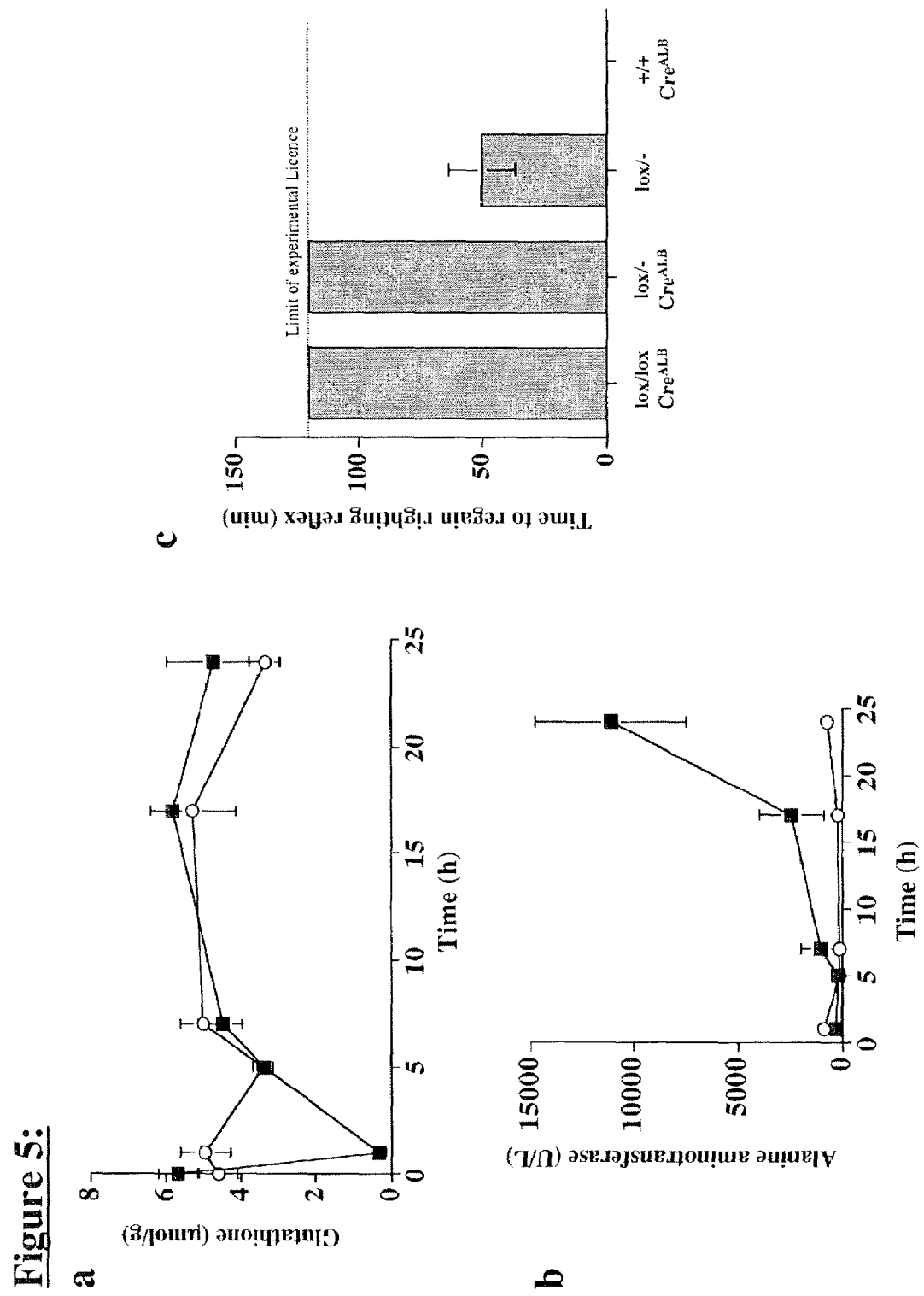

MODULATION OF CYTOCHROME P450 REDUCTASE ACTIVITY

RELATED APPLICATION

The present application claims priority from U.S. Provisional Application Ser. No. 60/410,057, filed Sep. 12, 2002, and Great Britain Application No. 0216203.0, filed on Jul. 12, 2002, the disclosures of which are hereby incorporated herein by reference in their entireties.

FIELD OF THE INVENTION

The present invention relates to the uses of non-human transgenic animals, tissues and/or cells derived therefrom having depleted or ablated cytochrome P450 reductase (CPR) expression, methods of producing such animals, tissues and/or cells, for use especially, but non exclusively, in both in vivo and in vitro screening of therapeutic agents, drug development and drug metabolism/disposition studies.

BACKGROUND TO THE INVENTION

Transgenic animals are characterized by the presence of exogenous or non-native DNA integrated into their genetic information. The animals express or do not express, as the case may be, the genetic characteristic encoded by the foreign DNA.

The hepatic cytochrome P450-dependent monooxygenase system plays a central role in mammalian defence against harmful environmental chemicals; it is also a major determinant of the half-life and pharmacological properties of therapeutic drugs and in certain cases, mediates the activation of drugs, toxins and carcinogens to their ultimate toxic species. Several other functions have been ascribed to hepatic P450s, including control of cholesterol and steroid hormone metabolism and bile acid biosynthesis. However, for certain of these pathways, the exact role of P450s in normal homeostasis is unknown.

There have been major advances in understanding the functions, genetics and regulation of these enzymes and more recently their structures. However, many fundamental questions about the role of these enzymes in normal homeostasis and in the metabolism and activity of drugs and chemical toxins remain to be answered. The size and diversity of the P450 multi-gene family results in great difficulties in dissecting out the function(s) of individual hepatic P450s, particularly as many of these enzymes involved in foreign compound metabolism exhibit overlapping substrate specificities. In order to understand the functions of this enzyme system an approach is required which will allow the simultaneous inactivation of large numbers of cytochrome P450s.

All cytochrome P450s located in the endoplasmic reticulum receive electrons from a single donor, Cytochrome P450 Reductase (CPR; NADPH:ferrihemoprotein reductase, EC 1.6.2.4);

conditional deletion of this protein could therefore inactivate all the P450s located in the endoplasmic reticulum in any particular cell type. It is known from the prior art that P450 expression during development is a vital requirement. In recent studies, although a complete deletion of CPR was achieved it was shown to be embryo lethal (1, 2).

A transgenic non-human animal and/or tissue and/or cells derived therefrom that can be used as a model to study the cytochrome P450-dependent monooxygenase system at a molecular and cellular level and all its associated interactions in drug/toxin metabolism and/or disposition would offer immediate advantages to the art and pharmaceutical, agrochemical, chemical and food industries in general and also permit a further understanding of many biochemical mechanisms.

STATEMENT OF THE INVENTION

According to a first aspect of the invention there is provided use in product development, disposition and/or toxicity studies and/or rationalised drug design of a non-human transgenic animal comprising cells with a conditional deletion of cytochrome P450 reductase gene.

Reference herein to "product" is intended to include a pharmaceutical, therapeutic, drug, toxin, agrochemical, chemical, food or cosmetic agent/molecule/moiety/ compound/complex or any other natural or synthetic chemical product which may be investigated using the animals or methods of the present invention.

In this specification, except where the context requires otherwise, the words "comprise", "comprises" and "comprising" mean "include", "includes" and "including" respectively. That is, when the invention is described or defined as comprising specific features, various embodiments of the same invention may also include additional features.

All publications, patent applications, patents and other references mentioned herein are incorporated by reference in their entirety.

According to a yet further aspect of the invention there is provided use of a non-human transgenic animal comprising cells with a conditional deletion of cytochrome P450 reductase gene in studying of disease states, modulation of hormone function and levels and other endogenous pathways and substrate metabolism in which P450s play a role.

According to a yet further aspect of the invention there is provided use of tissue(s) and or cell(s) derived from of a non-human transgenic animal comprising cells with a conditional deletion of cytochrome P450 gene as an in vitro screen in product development and/or disposition toxicity studies.

According to a yet further aspect of the invention there is provided a transgenic animal, tissues and/or cells derived therefrom as modified to contain or express DNA encoding a human DNA cytochrome P450 or another protein involved in product metabolism, chemical toxicity or other metabolic pathways.

According to a yet further aspect of the invention there is provided use of human cells introduced into an immune-deprived animal of the present invention so as to investigate contribution of said human cells to P450-mediated product metabolism and/or toxicity or other functions where the P450 system is involved.

DETAILED DESCRIPTION OF THE INVENTION

Animals suitable for carrying out the present invention are, in general, non-human animals, such as monkeys, dogs, cats, rabbits, rats and mice. Rodent species are preferred, and the mouse is the most preferred species. Animals in every stage of development, including embryonic, neonatal, juvenile, adolescent and adult are included in this description.

Reference herein to deletion of cytochrome P450 reductase (CPR) is intended to include partial or complete ablation, hepatic null or reductase null, "knock-out" or inability to express CPR, the animals having an endogenous CPR gene that can be deleted which may involve removal or all of part of the CPR gene. A reductase null animal may also include an animal where reductase expression is prevented for example by inhibition of CPR mRNA processing.

The term conditional deletion refers to the switching "on" or "off" of a particular gene, in this instance the CPR gene, which is conditional on a specific stimulus.

As previously discussed, hepatic cytochrome P450s play a key role in foreign compound metabolism and normal homeostasis. In order to investigate the functions of this multigene family of proteins we have carried out a conditional deletion of murine hepatic cytochrome P450 reductase. The experimental approach of the present invention has proved effective, resulting in almost complete ablation of hepatic P450 activity, and has generated some unexpected phenotypes. The mice of the present invention produce essentially no bile acids, and exhibit hepatic cholesterol and triglyceride accumulation which, counter-intuitively, is accompanied by a 60-70% reduction in circulating cholesterol and triglycerides.

We have also observed that the mice exhibit a profound reduction in their ability to metabolise drugs and become resistant to toxins activated by the P450 system. In spite of these profound changes, we have unexpectedly found that the animals of the present invention live and are able to reproduce normally, thus demonstrating that hepatic P450-mediated hormone metabolism is not essential for survival or fertility contrary to the teachings of the prior art. Thus, the animal model of the present invention will allow many of the outstanding and fundamental questions about this enzyme system, to be addressed and answered.

Cre is a 38 kDa recombinase protein from bacteriophage P1 which mediates intra and inter molecular site specific combination between loxP sites. The loxP site consists of 13 bp inverted repeats separated by an 8 bp asymmetric spacer region. One molecule of Cre binds per inverted repeat or two Cre molecules line up at one loxP site. The recombination occurs in the asymmetric region. Those 8 bp are also responsible for the directionality of the site. Two loxP sequences in opposite orientation to each other invert the intervening piece of DNA, two sites in direct orientation dictate excision of the intervening DNA between the sites leaving one loxP site behind so as to precisely remove the DNA.

The animals of the present invention may preferably be produced by a method comprising the steps of transfecting embryonic stem cells with a CPR targeting construct, selecting animals homozygous for a floxed CPR locus (CPR$^{lox/lox}$) and crossing said animals with a line where Cre expression is regulated.

Reference herein to regulation of Cre expression is intended to include constitutive and inducible regulation by either an endogenous or exogenous agent or stimulus.

Preferably, Cre expression is regulated by a promoter for example a rat albumin promoter or CMV promoter or CYP1A1 promoter.

It will be appreciated that in the instance of using a rat albumin promoter as the albumin promoter becomes active neonatally CPR expression and activity decreases to an extent where at 6 to 8 weeks of age there is no immunoreactive band corresponding to CPR. In this manner CPR expression is conditionally deleted by aging and remains deleted as a consequence of the continuous activity of the albumin promoter.

It will also be appreciated that site specific recombinase methods other than cre-recombinase will also be applicable to a method of producing the animals of the invention, for example using Flp/ftr. The Flp recombinase is a 45 kD protein encoded by the 2Mm plasmid of the yeast *Saccharomyces cerevisiae*. It would also be possible to use a C31/attB, attP or a gene trap vector.

According to a yet further aspect of the invention there is provided a CPR targeting construct covering exons 3 to 16 of a CPR gene.

Preferably, the construct comprises a 12 kb SalI fragment.

Preferably, the construct is included in a cassette, flanked by same-orientation loxP sites and optionally containing a selectable marker, for example, neomycin.

Preferably, the cassette also includes a promoter for example a herpes simplex thymidine kinase (hsv-tk) promotor.

Preferably, the casette is inserted into intron 4.

According to a yet further aspect of the invention there is provide use of the construct of the present invention in the production of an animal according to the present invention.

We have been able to generate mice where CPR is deleted in the post-natal period in any tissue, using by way of example only the Cre/loxP system (3). Hereinafter the intriguing phenotypes observed with a hepatic deletion of the enzyme system will be described.

It will be appreciated that other methods of deleting or ablating CPR or reducing/preventing its expression may also be applicable with the method of the present invention. For example such methods include, siRNA technology (small inhibitor RNA technology). siRNA refers to the introduction of homologous double stranded RNA (dsRNA) to specifically target a gene's product, resulting in null or heterozygote phenotypes or hypomorphic phenotypes.

It will be appreciated that the hepatic nulls or reductase null heterozygote animals of the present invention may in one aspect of the invention be used as an in vivo screen to determine any one or more of the following parameters:

(i) role of cytochrome P450s or cytochrome P450 reductase in the disposition of an organic, low molecular weight small molecule, preferably <1000Da. These studies can be carried out by the oral, dietary or intravenous administration of the compound to be tested and evaluation of the rates of elimination in the bile, urine or faeces or alternatively, by measuring circulatory levels of the compound. In addition, the level of metabolism or the disposition of a drug/compound in vivo could be determined by measuring the concentration of the drug/compound at different time points detected in different tissues, e.g. by using radio-labelled compound followed by whole body autoradiography or by analysis of drug/compound levels in a particular tissue e.g. using analytical methods such as mass spectrometry;

(ii) pathways of drug/product disposition. Deletion of P450 reductase in extrahepatic cells will allow the role of metabolism in drug uptake and intracellular drug concentration to be determined through pathways of drug disposition. By comparing the metabolites produced in control or P450 hepatic reductase null animals it will be possible to establish which metabolites are produced as a direct consequence of the activity of the hepatic cytochrome P450 system;

(iii) routes of Phase II drug/product disposition of a parent compound. In the absence of hepatic cytochrome P450 activity it will be possible to establish whether other enzymes are involved in the disposition of the parent compound. This may not be immediately obvious in the control animals, where the situation is complicated by P450-mediated reactions;

(iv) role of drug transporters in drug uptake across for example, the gastro-intestinal tract and, into the liver. In the absence of cytochrome P450 expression in tissues such as the liver or the GI tract the evaluation of the role of other enzymes or proteins in determining drug bioavailability, in particular the role of drug transporters will be facilitated. At the present time, most of the inhibitors of drug transporters are also inhibitors of the cytochrome P450 system. The use of such compounds in vivo to study their effects on drug bioavailability or metabolism does not allow the investigator to distinguish one pathway from another. However, in the absence of P450 activity there is greater confidence that the inhibitors are now specific for the drug transporters and therefore studies on the role of drug transporters in determining bioavailability will become feasible using the animals of the present invention;

(v) role of cytochrome P450 reductase in pathways of chemical toxicity. The cytochrome P450 system can detoxify drugs and foreign compounds through metabolism, e.g, in the case of many anticancer drugs and it can also catalyze the conversion of many compounds to products which are chemically reactive and toxic. The conditional reductase null model of the present invention may be used to evaluate the role of the P450 system in these reactions. Identification of a role for P450s in these reactions will advantageously permit studies to be carried out to evaluate whether such reactions are relevant to man and also will facilitate the redesign of the molecules to avoid these unwanted effects;

(vi) role of the P450 system in normal metabolic processes/homeostasis. In addition to its role in drug disposition the cytochrome P450- dependent mono-oxygenase system carries out a large number of important metabolic functions, some of the consequences of these reactions are unknown. The P450 reductase animal model of the present invention may advantageously be used to delete cytochrome P450 function in a tissue- or cell-specific manner to establish the role of particular P450 pathways in normal homeostasis. This will allow an evaluation of whether these particular pathways, for example and without limitation, retinoic acid metabolism in the skin or neurosteroid biosynthesis in the brain, provide novel targets for the development of new drugs. In addition, the potential ablation of cytochrome P450 activity will allow novel disease models to be generated, for example and without limitation, deletion of the Vitamin D1,25-hydroxylase activity in the liver and kidney will generate a Vitamin D-deficient mouse, deletion of steroid hormone biosynthesis in the adrenal will generate a mouse deficient in steroid hormones. Therefore, in one embodiment of the invention the P450 reductase null animal may be used to generate disease models for the potential testing of new drugs which may be therapeutic against the phenotypes observed;

(vii) role of the P450 system in the pathogenesis of disease. Because of the role of the cytochrome P450 system in normal homeostasis, the P450 reductase null mouse model may be used to evaluate the role of the P450 system in disease aetiology and progression. This would find particular utility in degenerative diseases where the cytochrome P450 system is known to have the capacity to generate chemically reactive oxygen species that may potentiate degenerative processes.

It will be appreciated that the hepatic nulls or reductase null heterozygote animals of the present invention may also in one aspect of the invention be used as an in vivo screen to investigate any one or more of the following events or parameters:

(i) pharmacological potency of agents subject to first pass metabolism, i.e. which would otherwise have been metabolised. With some drugs in development it is not possible to establish their in vivo pharmacological activity because high rates of first-pass cytochrome P450 mediated metabolism do not allow sufficient concentrations to be obtained to measure a pharmacological effect. This may result in valuable and potent compounds not being developed. However, in the hepatic reductase null mice of the present invention, for such compounds high drug levels may be obtainable and their pharmacological potency evaluated. In the event that the compound demonstrates in vivo potency the compound could subsequently be modified to circumvent the high rates of P450 metabolism;

(ii) occurrence and rate of extrahepatic metabolism in for example and tissues such as and without limitation kidney, brain, GI tract, skin and/or adrenal gland. It has been estimated that up to 30% of drug metabolism may occur in tissues other than the liver and may well vary according to the specific drug involved. The rate of extra hepatic drug metabolism may be an important parameter in drug disposition/toxicity as well as in altering susceptibility to events such as drug-drug interactions. The hepatic P450 reductase null mouse of the present invention could therefore be used to establish whether any particular drug or chemical entity is metabolised in extrahepatic tissues and what that rate of metabolism is. Extrahepatic metabolism may also be an important parameter for the activation of pro-drugs in particular cell types in order for them to exert their therapeutic activity, accordingly the animals of the present invention may find utility in pro-drug activation studies;

(iii) rate of hepatic metabolic clearance as a determinant in product/drug distribution and pharmacokinetics. Establishing the rate of metabolic clearance is a key pharmacokinetic parameter which determines the biological half-life and activity of therapeutic agents and foreign chemicals. In the absence of P450 metabolism the role of these enzymes in metabolic clearance can be clearly established and will allow a better understanding of how potential drugs or compounds may be handled in man;

(iv) facilitate in lead product/compound- selection based on in vivo metabolic parameters. Based on metabolic parameters, the hepatic P450 reductase null mouse of the present invention may be used as a tool in the rapid screening of large numbers of chemical entities to establish which have the most appropriate pharmacokinetic parameters for use in man. It would also identify compounds which require chemical modification in order to optimise their pharmacokinetic properties;

(v) cross into drug discovery mouse models so as to establish the effects of metabolism on pharmacological activity and therapeutic outcome. It is known from the prior art that an increasing number of transgenic reporter mice are being developed for pre-clinical drug development, toxicology and drug discovery purposes. In one embodiment of the invention the hepatic reductase null model may be advantageously crossed into one of these reporter mouse systems, thereby allowing a much clearer evaluation of the role of metabolism on the pharmacological or toxicological effects of a compound under investigation;

(vi) assessment of relevance and occurrence of pharmacologically active metabolites. Many products/drugs first require metabolism by the cytochrome P450 system to generate pharmacologically active products. It is also important to evaluate whether the metabolism of a potential drug or product results in inactivation or whether the product retains or even has enhanced pharmacological or toxicological properties. Comparison of pharmacological effects in animals which do or do not contain P450 metabolism will allow an evaluation of prodrug or chemical activation to be established;

(vii) distinguish between toxicity due to product metabolic activation or other mechanisms. Many chemicals agents are toxic as a consequence of their conversion to reactive metabolites by the cytochrome P450 system. In the event that a drug or product in development exerts an idiosyncratic toxicity in vivo the conditional P450 reductase null mouse may be used in one embodiment of the invention to evaluate whether metabolic activation by the cytochrome P450 system is involved. If this is the case, the nature of the toxic metabolites can be established and the molecule redesigned to avoid such potentially toxic events;

(viii) establish role of P450 or P450 reductase as a rate-limiting step in drug/compound disposition. In addition to using conditional deletion of reductase in a particular cell type experiments maybe carried out in mice heterozygous for P450 reductase expression, i.e. mice are bred which contain one P450 reductase null allele and a functional P450 reductase allele. Under these circumstances, P450 activity would be predicted to be reduced as a consequence of a limited rate of electron flow to the P450 enzymes. Evidence that this is the case has already been obtained, therefore this particular model of the invention may be used to establish the role of the P450 system in the parameters described above. In the event that the metabolism of a drug is not altered in the P450 reductase heterozygous mice, this will indicate that electron transfer to the P450 system is not an important determinant in the rate of drug disposition;

(ix) role of bile flow on drug elimination. The hepatic P450 reductase null mice of the present invention have been shown to have compromised bile acid production. The animals of the present invention may therefore be used to establish the effects of bile flow on the rate and pathways of drug disposition. Such studies may be particularly valuable for compounds which cause choleostasis; or (x) study drug/drug interactions due either to P450 or drug transporter effects. As described above, if hepatic P450 activity is absent it would be possible to carry out drug-drug interaction studies in order to evaluate whether such effects are due to interaction with the cytochrome P450 system or with other pathways of drug uptake and disposition, such as with the drug transporters. Such information is important both for drug regulatory purposes and for identifying potential difficulties in the use of a drug in the clinic.

It will be appreciated that the hepatic nulls or reductase null heterozygote animals of the present invention may also in one aspect of the invention be used in any one or more of the additional following situations:

(i) as a cross into a disease model so as to establish the role of compound metabolism in pharmacological/toxicological effects of the product;

(ii) as a cross into a multi drug response protein (Mdr1 and Mdr2) null mouse so as to evaluate a dual role of both P450s and Mdr in product availability studies;

(iii) as a cross into reporter animals, for example and without limitation oxidative stress sensitive reporters for the study of degenerative diseases. Crossing the conditional reductase nulls of the present invention into mice carrying reporters for specific diseases will allow the role of the P450 system in the etiology and progression of that disease to be evaluated. The reductase null mice can also be crossed into reporter mice, e.g. which reflect particular types of cellular stress responses so that the role of the P450 system in metabolic activation of a chemical and mechanism of the toxic effects can be established more easily. In addition, many drugs and foreign compounds have the capacity to induce or suppress the cytochrome P450 system. In many cases whether this effect is due to the parent compound or to one of its metabolites is unknown. This is particularly the case e.g. for chemopreventive agents. In one example of this embodiment of the invention, a reporter system may be used, e.g. where the promoter of a gene is linked to a reporter such as LacZ, alternatively in a toxicology screen the promoter could be activated by a chemical as in the case of the CYP1A1-LacZ system;

(iv) in generating cell lines from the animals of the present invention, with no P450 reductase activity, e.g. fibroblasts or by introducing an immortalizing gene, e.g. SV40 T antigen, for any cell type. In addition to the in vivo experiments, all the experiments described above could be carried out in vitro. These could be carried out either using primary cells derived from the conditional hepatic reductase null mice or from cell lines derived from them, e.g. by using fibroblast cell lines or by introducing an immortalizing gene into the cells, either by crossing the reductase mice into mice carrying an immortalizing gene such as SV40 large T antigen or by introduction of the immortalizing gene to the primary cells in culture; or (v) in generating novel in vivo mutation tests so as to evaluate the role of P450/P450 reductase in chemical mutagenesis. An important aspect of chemical and drug development is to establish whether the chemical entity has toxic or particularly mutagenic potential. In vivo, the P450 reductase null mice could be crossed into mice which report mutagenic events such as big blue mice to establish the role of the P450 system in chemical mutagenicity. Alternatively, in vitro studies could be carried out using hepatic sub-cellular fractions from control or reductase null animals to establish the role of P450 metabolism in any mutagenic effect observed, e.g. using S9 fractions in the Ames test.

The cytochrome P450-dependent monooxygenase system is distributed throughout the body and different enzymes are expressed in a tissue- and cell-specific manner. In one embodiment of the invention the Cre recombinase system is specifically targeted in a conditional way to particular cell types to enable the specific deletion of particular enzymes in those cells. This may be achieved preferably by the use of the promoters of cytochrome P450 genes or promoters of other drug metabolising enzymes to drive Cre recombinase so as to direct expression to cells containing these enzymes. In addition, the promoters of transcription factors which mediate the regulation of cytochrome P450 genes may preferably be used as a mechanism of delivering Cre specifically to cells where particular P450 enzymes are expressed.

According to a yet further aspect of the invention there is provided an animal or an animal cell comprising a Cre recombinase system and a promoter for driving expression of Cre recombinase in a tissue or cell specific manner, the promoter being selected from the group comprising a cytochrome P450 promoter, a promoter of another drug metabolising enzyme or a transcriptional factor promoter.

Cytochrome P450 CYP1A1 is a highly regulatable gene whose expression is determined by the presence of xenobiotic responsive elements contained within the promoter. We have previously demonstrated that this promoter provides an extremely tight on/off switch for regulating gene expression in response to exogenous chemical agents i.e. constitutive levels of cytochrome P4501A1 are extremely low but are highly inducible on exposure of animals or cells to a range of specific chemical entities. CYP1A1 is regulatable in virtually all cell types expressing the cytochrome P450 system, accordingly in one embodiment of the invention administration of an exogenous agent causes deletion of the P450 system in virtually all relevant cells of the animal. Therefore, crossing P450 reductase floxed mice with CYP1A1 Cre mice will allow the conditional regulation of Cre in many cell types. In other embodiments of the invention, a transcriptional factor promoter such as the pregnane x-receptor (PXR) promoter is used to generate tissue-specific conditional deletions. This receptor is predominantly expressed in liver, intestine and kidney and therefore the promoter using this to drive Cre recombinase would allow specific deletion of the P450 system in these tissues. A further alternative is the promoter of the transcription factor, Nrf2, which again is regulated by a distinct class of compounds such chemopreventive agents including coumarin, ethoxyquin and butylated hydroxyanisole. A yet further example is the cytochrome P450 CYP2B1 or CYP2B6 promoter which would provide constitutive expression in the alveolar type 2 cells and clara cells of the lung as well as regulatable expression specifically in the liver by a range of compounds including barbiturate drugs. Additionally, the use of the cytochrome P450 CYP3A or CYP4A promoters would allow regulation of Cre in the liver or intestine by compounds such as dexamethasone or clofibric acid respectively. Accordingly, in these particular embodiments of the invention a promoter such as hereinbefore described is used for tissue/cell specific Cre expression in a constitutively or inducible manner so that specific tissue/cells may comprise a CPR gene deletion.

In one embodiment of the invention, the reductase null animals of the present invention may advantageously be used to delete the P450 system in a tissue or cell specific manner. Such animals may be used for the applications hereinbefore described, where the role of the P450 system in product/drug metabolism, detoxification, normal homeostasis or in disease etiology is to be studied. It is envisaged that this embodiment will also allow other effects, such as drug transporter-mediated effects, to be studied in those tissues or cells in the absence of metabolism.

Preferably, tissue specific deletions are achieved by crossing CPR-floxed mice into mice where cre recombinase is driven off a tissue- or cell-specific promoter, for example that of an intestinal fatty acid binding protein, so as to obtain a GI tract specific deletion or in another example, bovine keratin VI, so as to obtain a skin epithelial cell deletion.

As previously mentioned, Cre regulation may be constitutive or inducible. In another embodiment of the invention, the regulation of cre may be conditional, that is to say its expression can be regulated by the administration of an exogenous agent, for example and without limitation by using the tamoxifen switch system, or the tetracycline inducible expression system. One such example is where cre is driven off the CYP1A1 promoter which is regulated by a large number of exogenous foreign compounds. Cre recombinase activity is silent until the exogenous inducing agent is applied, i.e. there is no phenotype observed until this is done. Accordingly, it is envisaged, in an in vivo experiment this would advantageously allow the same animal to be used as both test and control. The CYP1A1 system may be used to obtain a liver predominant deletion or a deletion in adult or fetal tissue where the CYP1A1 promoter is active. The tissue/cell specific or the pan-deletion may be used in product/drug development, disposition and toxicity studies as hereinbefore described.

The cytochrome P450 system, in addition to its role in drug and foreign compound metabolism, plays an important role in the biosynthesis and metabolism of a range of hormones and signalling molecules in a variety of different tissues. For example, in steroid hormone biosynthesis (estrogens, prostacyclins, androgens, glucocorticoids) in the gonads and adrenal glands, arachadonic acid metabolism in the kidney, thromboxane in platelets, prostaglandin metabolism in the lung and prostate gland, Vitamin D3 metabolism in the liver and kidney, neurosteroid biosynthesis/metabolism in the brain and hypocampus, catechol estrogen biosynthesis in adrenal glands, fetal liver and hypothalamus, bile acid biosynthesis in the liver, fatty acid metabolism in the liver and lungs and retinoic acid metabolism in the fetus, liver and skin. In addition P450s play an important role in pregnancy and fetal development therefore the present invention provides a tool with which to study their role in these conditions.

Accordingly the animals of the present invention, in a further aspect of the invention may be used to modulate the functions and the levels of associated hormones in any of the above cell types to generate a disease model or a model for product/drug discovery or a model to verify or assess functions of the P450 system.

We have observed that deletion of hepatic P450 reductase resulted in almost complete ablation of bile acid production the major route of cholesterol disposition, and that this was accompanied by a significant hepatic accumulation of cholesterol. Surprisingly and contrary to expectation however it was also accompanied by a reduction in circulating cholesterol levels, thus identifying a hitherto unidentified role for the P450 system in controlling both hepatic and circulating cholesterol levels.

With these observations in mind, in a yet further aspect of the invention there is provided use of the animals of the present invention in assessing the role of bile acids in disease states and in drug disposition studies, as a model for studying choleostasis, assessing the role of cholesterol in atherogenesis and other disease states.

According to a yet further aspect of the invention there is provided use of the animals of the present invention in identifying novel drugs which inhibit the P450 system and which may also be used to reduce circulating cholesterol levels.

According to a yet further aspect of the present invention there is provided use of the animal tissues and/or cells derived therefrom of the present invention as an in vitro assay for the study of any one or more of the following events/parameters:

(i) role of transporters in product uptake and efflux;
(ii) identification of product metabolites produced by the cytochrome P450 system;
(iii) evaluate whether candidate products are P450 substrates;
(iv) assess drug/drug interactions due to P450 effects;
(v) cross into Mdr1 and/or Mdr 2 null mice so as to evaluate a dual role of P450s and Mdr or;
(vi) use of an S9 fraction from null mice in an Ames test so as to determine potential P450-mediated chemical mutagenicity.

Reference herein to animal tissues and/or cells derived therefrom is intended to include primary hepatocytes, hepatic cell lines, hepatic microsomal fractions, liver slices, and/or any other tissue, for example and without limitation, kidney, lung or brain tissue and/or cells, for example and with out limitation, keratinocytes or chondrocytes in which, under normal conditions cytochrome P450 and/or cytochrome P450 reductase is expressed and/or transported thereto or therefrom.

The tissue and/or cells of the present invention being derived from the animals of the present invention or manufactured in vitro or ex vivo, all of which are encompassed within the scope of the present invention.

It will be appreciated that tissue and/or cells derived from the hepatic nulls or reductase null heterozygote animals of the present invention may also in one aspect of the invention be used as a tool/screen to investigate any one or more of the following events or parameters:

(i) establish involvement of the cytochrome P450 system in hepatotoxicity/carcinogenicity;
(ii) establish whether hepatic product metabolism is involved in toxicity to other organs;
(iii) establish whether hepatic production of a product metabolite (i.e. prodrug activation) is important for phannacological action/toxicity of a given candidate compound;
(iv) establish whether a parent product or its P450 generated metabolite(s) mediate induction of drug metabolising enzymes, liver growth or other phenotypic effects;
(v) investigate role of the P450 system in peroxisome proliferation;
(vi) investigate role of cytochrome P450 reductase in product disposition, toxicity or metabolic activation or;
(vii) investigate presence of secondary sites of toxicity in the absence of toxicity due to P450 mediated compound metabolism.

According to a yet further aspect of the invention there is provided a transgenic animal, tissues and/or cells derived therefrom as hereinbefore described, modified to contain or express DNA encoding a human a cytochrome P450 DNA.

According to a yet further aspect of the invention there is provided use of a transgenic animal, tissues and/or cells derived therefrom that has been modified to contain and express DNA encoding a human DNA cytochrome P450 so as to establish the role of human P450s in foreign or endogenous compound metabolism, toxicity or normal homeostasis.

According to a yet further aspect of the invention there is provided use human cells, especially hepatocytes introduced into an immuno-deprived reductase null animal of the present invention so as to investigate contribution of human cells or hepatocytes in P450-mediated product metabolism and/or toxicity.

In this embodiment of the invention, human cells or hepatocytes may grow in, for example the liver or spleen of SCID (severe combined immune deficiency) mice. SCID mice are homozygous for the Prkd$^{scid}$ mutation and lack both T and B cells due to a defect in V(D)J recombination. Therefore, these mice easily accept foreign tissue transplants, including human tumors, making them effective models for testing new cancer treatments and as hosts for human immune system tissues (i.e., SCID-hu).

Accordingly, in this embodiment of the invention only the human cells or hepatocytes will contribute to cell or hepatocyte-mediated P450 metabolism and thus may be advantageously used as a human metabolism model in the absence of background mouse metabolism.

According to a yet further aspect of the invention there is provided a method of introducing a human cytochrome P450 into an animal cell or cells whose own endogenous P450 is compromised due to reductase deletion, the method comprising introducing a human P450 alone or in combination, for example as P450 reductase fusion protein, where the introduced P450 reductase is tightly coupled to a specific P450 into an animal cell.

The fusion of CYP3A4 or CYP2D4 to P450 reductase generates functional P450 enzymes. Thus, such a fusion driven off a suitable gene promoter, for example CMV or a tissue or a specific promoter such as rat albumin or CYP1A, and introduced into transgenic mice will provide an expression of the fusion protein in a constitutive or conditional fashion.

In one embodiment of the method, in order to avoid trans-electron transfer from the P450 reductase in the fusion (or where separate human P450 and P450 reductase polypeptides are used) to the murine P450s the fusion protein could, for example, be targeted to a specific cellular compartment where murine P450s are not expressed, i.e. in another cell type such as the spleen or in a different cell compartment altogether, such as the cytoplasm or plasma membrane of hepatocytes.

Preferably, a targeting sequence is added to the fusion protein or a tissue specific promoter to drive the P450 expression.

According to a yet further aspect of the invention there is provided use of a transgenic animal, tissues and/or cells derived therefrom as hereinbefore described that have been modified to contain and express DNA encoding a human DNA protein so as to establish the role of said protein in a P450 metabolism free environment.

In this particular embodiment of the invention other human proteins of interest, for example and without limitation, drug transporters, may be introduced onto the Mdr/reductase null background of the animal or animal cells of the present invention and thus advantageously permit the functions of the human Mdr proteins to be studied on a P450 metabolism free or murine Mdr null background.

According to a yet further aspect of the invention there is provided a method of monitoring disease progression. Such method involves use of a transgenic non-human mammal, wherein the method comprises providing a transgenic non-human mammal produced by crossing a first parent carrying a hereditable disease determinant with a second parent carrying a hereditable deletion mutation of a cytochrome P450 reductase (CPR) gene, with the transgenic non-human mammal carrying and expressing both said disease determinant and the CPR deletion; and then (b) monitoring the progression of the disease in the mammal to determine the effect of cytochrome P450 metabolism on the progression of the disease. Diseases of interest include, but are not limited to, rheumatoid arthritis, atherosclerosis, neurodegeneration, obesity and cancer. Disease progression may be monitored in various tissues or cells. Exemplary tissues or cells may be derived from organs or organ systems such as the liver, kidney, lung, gastrointestinal system, brain, and skin.

Use of animal models is well known in the art and various animal models are described in PCT Application WO 02/35923; D. Hanahan, Nature, 406, 573-574 (2000); S. Artandi et al., Nature, 406, 573 (2000); U.S. Pat. No. 6,066,778 to Ginsburg et al.; U.S. Pat. No. 5,767,337 to Roses et al.; PCT Application WO 97/05247; L. Su et al. , Science, 256 (5060):1114 (1992); L. Su et al. , Science, 256(5057):668-70 (1992) M. Gurney et al., Science, 264: 1772-1775, (1994); C. Epstein et al., Proc. Natl . Acad. Sci. USA, 84: 80448048 (1997); A. Leder et al., Proc. Natl. Acad. Sci. USA, 87: 9178-9182 (1990); Leptin/OB, Cytokine Mini-reviews, @ (www.rndsystems.com/asp/g_sitebuilder.asp?bodyId=213 (R&D systems, 2002); T. Kowalewski et al., Proc Natl Acad Sci USA 96:3688-3693 (1999); A. Fagan et al., J. Biol. Chem, 274: 30001-30007 (1999); B. Han et al., Neurobiology of Disease 7:38-53 (2000); D. Holtzman at al., Proc. Natl. Acad. Sci. USA, 97:2892-2897 (2000); D. Holtzman et al., Ann Neurol 47:739-747 (2000); A. Fagan et al., Ann. Neurol. 48:201-210 (2000); B. Han et al., Nature Med. 7:338-343 (2001); R. DeMattos, Proc. Natl. Acad. Sci.

USA 98: 8850-8855:10.1073/pnas.151261398 (2001); J. Breslow, Proc. Natl. Acad. Sci USA, 90: 8314-83-18 (1993); D. Ishibashi et al., J. Clin. Invest. 92: 883-893 (1993); N. Maeda, Current opinion in lipidology, 4: 90-94 (1993); Y. Nakashima, ArterioslcerThromp,14: 1335 140 (1994); A. Plump et al., Cell, 71: 343-353 (1992); R. Reddick et al., Arterioscler Tromb. 14:141-147 (1994); S. Zhang et al, Science 258: 468-471 (1992); and S. Ishibashi et al., Proc. Natl. Acad. Sci USA 91: 4431-55 (1994), the disclosures of each of which are incorporated by reference herein in their entireties.

According to yet a further aspect of the invention there is provided a transgenic non-human mammal produced by crossing a first parent carrying a hereditable disease determinant with a second parent carrying a hereditable deletion mutation of a cytochrome P450 reductase (CPR) gene, with the transgenic non-human mammal carrying and expressing both the disease determinant and the CPR deletion.

According to yet a further aspect of the invention there is provided a method of determining whether an antitumor effect of a drug is due to the drug as given or a metabolite thereof, wherein the method comprises the steps of providing a transgenic non-human mammal produced by implanting tumor cells into a transgenic non-human animal carrying and expressing a deletion of a cytochrome P450 reductase (CPR) gene, administering a test compound to the mammal; and then determining the effect of the test compound on the proliferation of the tumor cells to thereby indicate whether the efficacy of the compound is due to the test compound as administered or a metabolite thereof, with less efficacy of the test compound on the transgenic non-human mammal as compared to a control mammal into which the tumor cells are implanted but which control mammal does not carry and express a conditional deletion of a CPR gene indicating that the effect of the test compound on the tumor cells is due to a metabolite of the drug. The antitumor effect may be determined in various tissue or cells. Exemplary tissues or cells may be derived from organs or organ systems such as the liver, kidney, lung, gastrointestinal system, brain, and skin.

According to yet a further aspect of the invention there is provided a transgenic non-human mammal produced by implanting tumor cells into a transgenic non-human mammal carrying and expressing a conditional deletion of a cytochrome P450 reductase (CPR) gene.

According to yet a further aspect of the invention there is provided method of screening for compounds useful for treating atherosclerosis, comprising providing a transgenic non-human mammal carrying and expressing a conditional deletion mutation of a cytochrome P450 reductase (CPR) gene, administering a test compound to the mammal; and then monitoring the mammal for the development or progression of atherosclerosis, wherein less development or progression of atherosclerosis in the mammal as compared to a control mammal that does not carry and express the conditional deletion indicates the test compound may be useful for treating atherosclerosis.

In preferred embodiments of the present invention as described above and below, the transgenic non-human animal or mammal is a monkey, dog, cat, rabbit, hamster, rat, or mouse. More preferably, the transgenic non-human animal or mammal is a mouse.

It will be appreciated that the present invention provides a tool for the investigation of disease states such as choleastasis, artherogenesis, hormonal unbalances, neurological disorders, degenerative diseases, skin conditions, cardiovascular disease, cancer and glaucoma and any other disease in which P450s play a role.

The invention will now be described by way of example only with reference to the following figures wherein:

FIG. 5 illustrates drug treatment of hepatic CPR null mice.

DETAILED DESCRIPTION OF THE FIGURES

Figure 1:
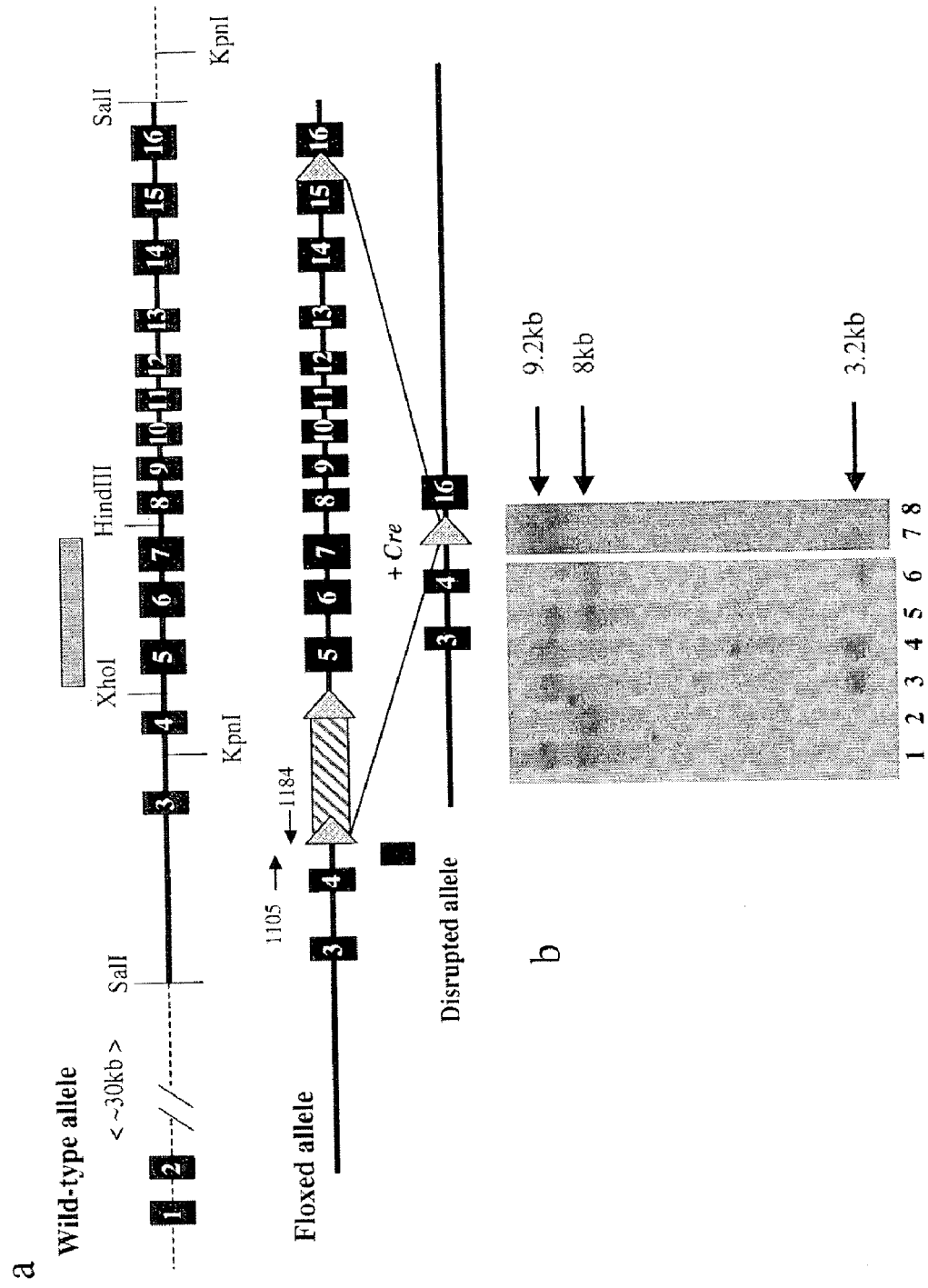
FIG. 1 illustrates targeting of the mouse CPR gene.
Figure 2:
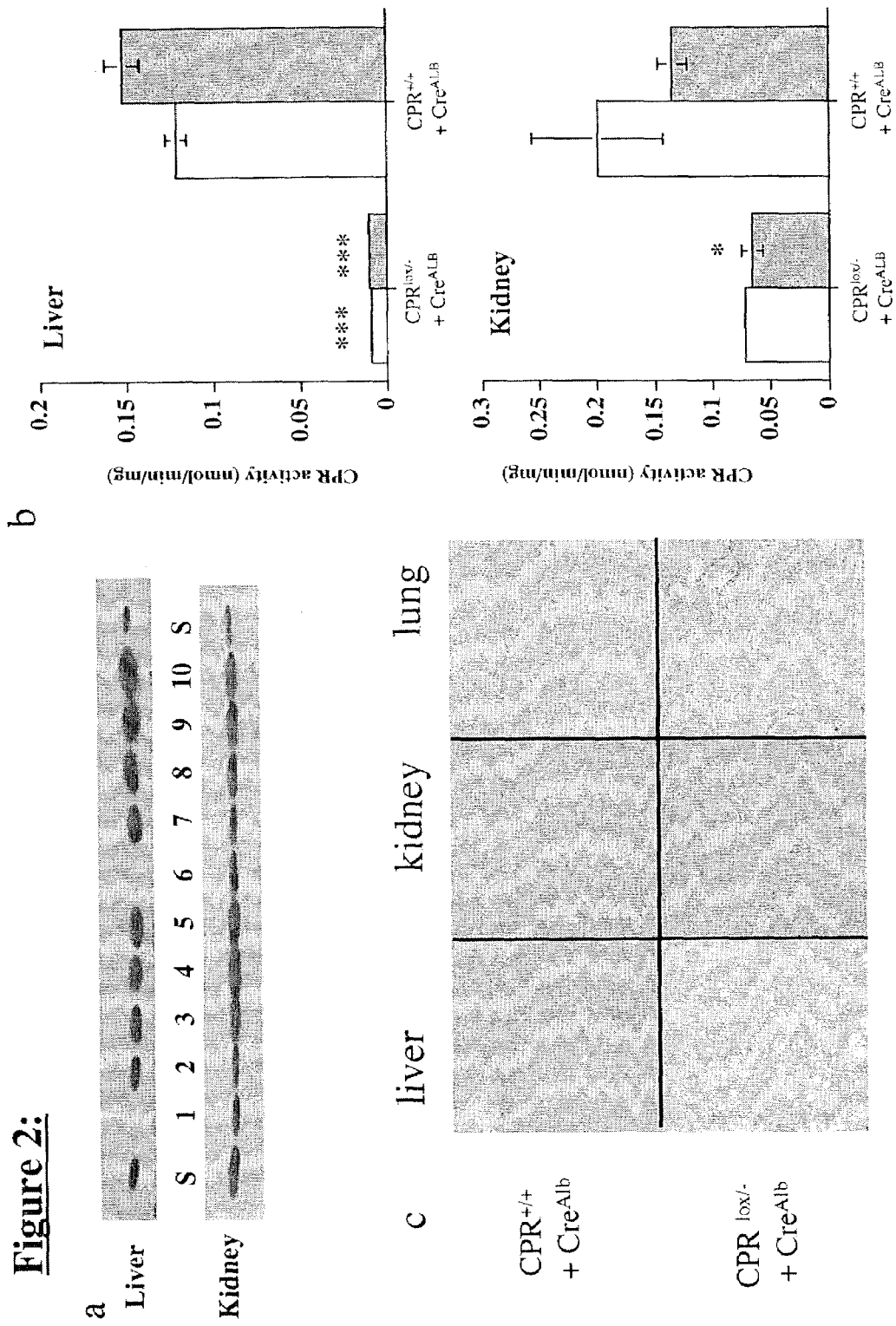
FIG. 2 illustrates liver-specific deletion of CPR in hepatic CPR null mice.

FIG. 1: Targeting of the Mouse CPR Gene.

a Maps of the wild-type, floxed and disrupted CPR alleles. A 12 kb SalI fragment, containing exons 3-16 of the mouse CPR gene was cloned and used for gene targeting. Exon I (untranslated) and exon 2 reside approximately 30 kb upstream, and are shown only for information. LoxP sites are indicated by triangles, and the selectable marker (hsv-tk-neo) is indicated by the hatched box in intron 4.

b Southern analysis of tail DNA from $CPR^{+/+}$, $CPR^{+/-}$, $CPR^{lox/+}$, $CPO^{lox/-}$ and $CPR^{lox/lox}$ mice. Genomic DNA was digested with KpnI and hybridised with a 1.5 kb XhoI-HindIII fragment as shown in a. The wild-type allele ($CPR^+$) is represented by a fragment of 8 kb, the targeted allele ($CPR^{lox}$, which also contains the selectable marker cassette), by a fragment of approximately 9.2 kb, whilst the deleted allele ($CPR^-$) is represented by a fragment size of 3.2 kb. Lanes 1,5 $CPR^{lox/+}$; Lanes 3,4=$CPR^{lox/-}$; Lane 2=$CPR^{+/+}$; Lane 6=$CPR^{+/-}$; Lanes 7,8=$CPR^{lox/lox}$;

FIG. 2: Liver-specific Deletion of CPR in Hepatic CPR Null Mice a Representative immunoblot showing CPR protein levels in liver and kidney of the following mice-lanes 1,6=CPR $^{lox/-}$+CreALB male, female; lanes 2,7 =$CPR^{lox/-}$ male, female; lanes 3,8=$CPR^{lox/+}$+$Cre^{ALB}$ male, female; lanes 4,9=$CPR^{lox/+}$ male, female; lanes 5,10=$CPR^{+/+}$+$Cre^{ALB}$ male, female; S=CPR standard b Hepatic and renal CPR activity in male (white bar) and female (grey bar) wild-type ($CPR^{+/+}$+$Cre^{ALB}$) and hepatic CPR null mice ($CPR^{lox/-}$+$Cre^{ALB}$), (n=3). Values are expressed nmol cytochrome c reduced/min/mg microsomal protein±SEM.

* p<0.05, *** p<0.001 using an unpaired t-test.

c Immunostaining of liver, kidney and lung sections from wild-type ($CPR^{+/+}$+$Cre^{ALB}$) and hepatic CPR null mice ($CPR^{lox/-}$+$Cre^{ALB}$) with anti-CPR antiserum. Data shown is representative of that found in each group (n=3).

Figure 3:
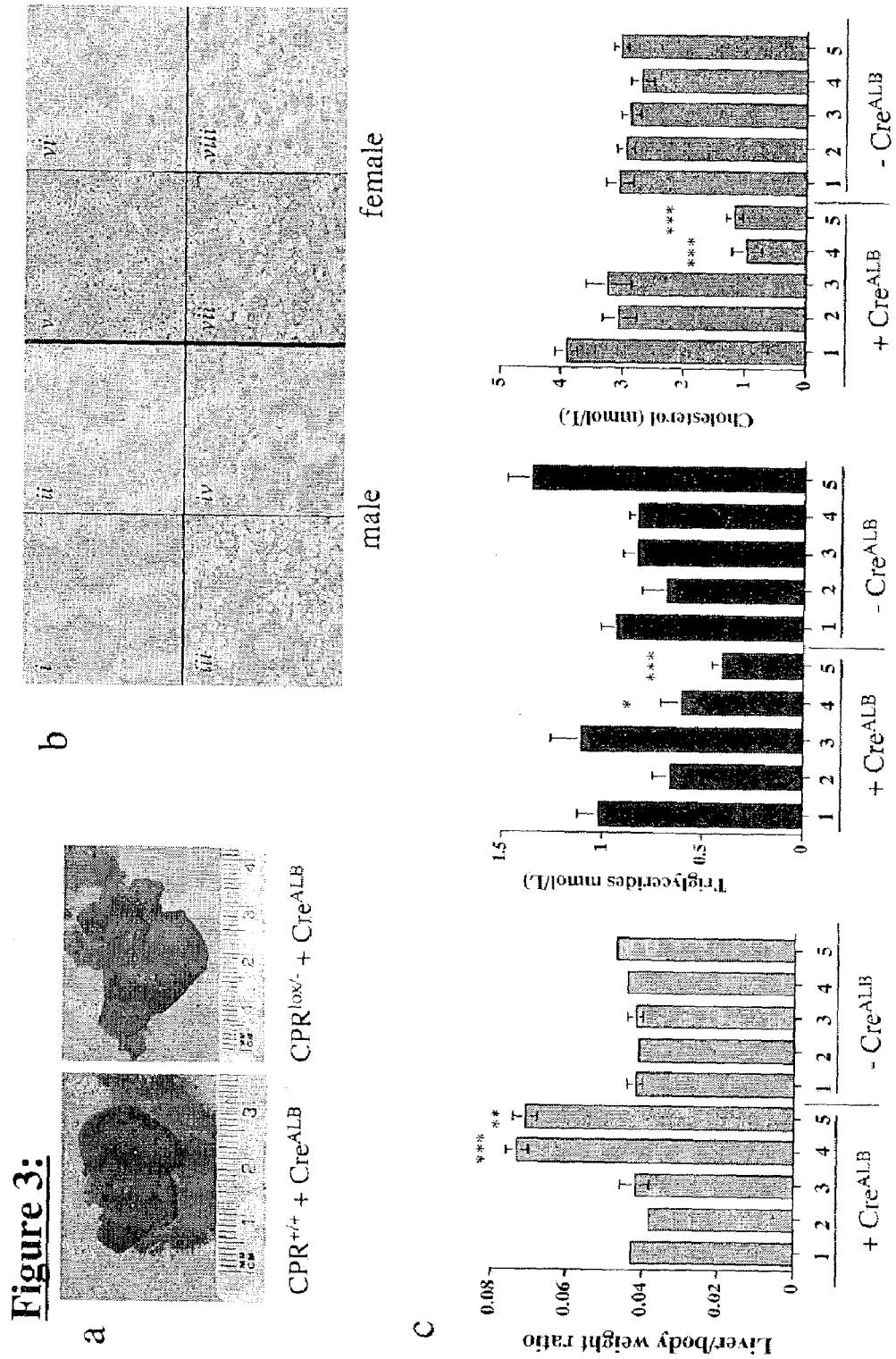
FIG. 3 illustrates characterisation of hepatic CPR null phenotype.

FIG. 3: Characterisation of Hepatic CPR Null Phenotype a Photographs show typically enlarged size and pale appearance of liver from hepatic CPR null mouse (right) and wild-type mouse (left).

b Representative sections from livers of male (left) and female (right) $CPR^{+/+}$+$Cre^{ALB}$ (top) (control) and $CPR^{lox/-}$+$Cre^{ALB}$ CPR null, (bottom) mice, stained with haematoxylin and eosin (i, iii, v, vii) or Oil Red 0 (ii, iv, vi, viii).

c Liver/body weight ratio, serum triglycerides and cholesterol in adult hepatic CPR null and wild-type mice (n=4-12). Values are expressed as mean±SEM. Lanes 1=$CPR^{+/+}$; 2=$CPR^{lox/+}$; 3=$CPR^{+/-}$; 4 =$CPR^{lox/-}$; 5=$CPR^{lox/lox}$.

* p<0.05,  p<0.005, * p<0.001 using an unpaired t-test.

Figure 4:
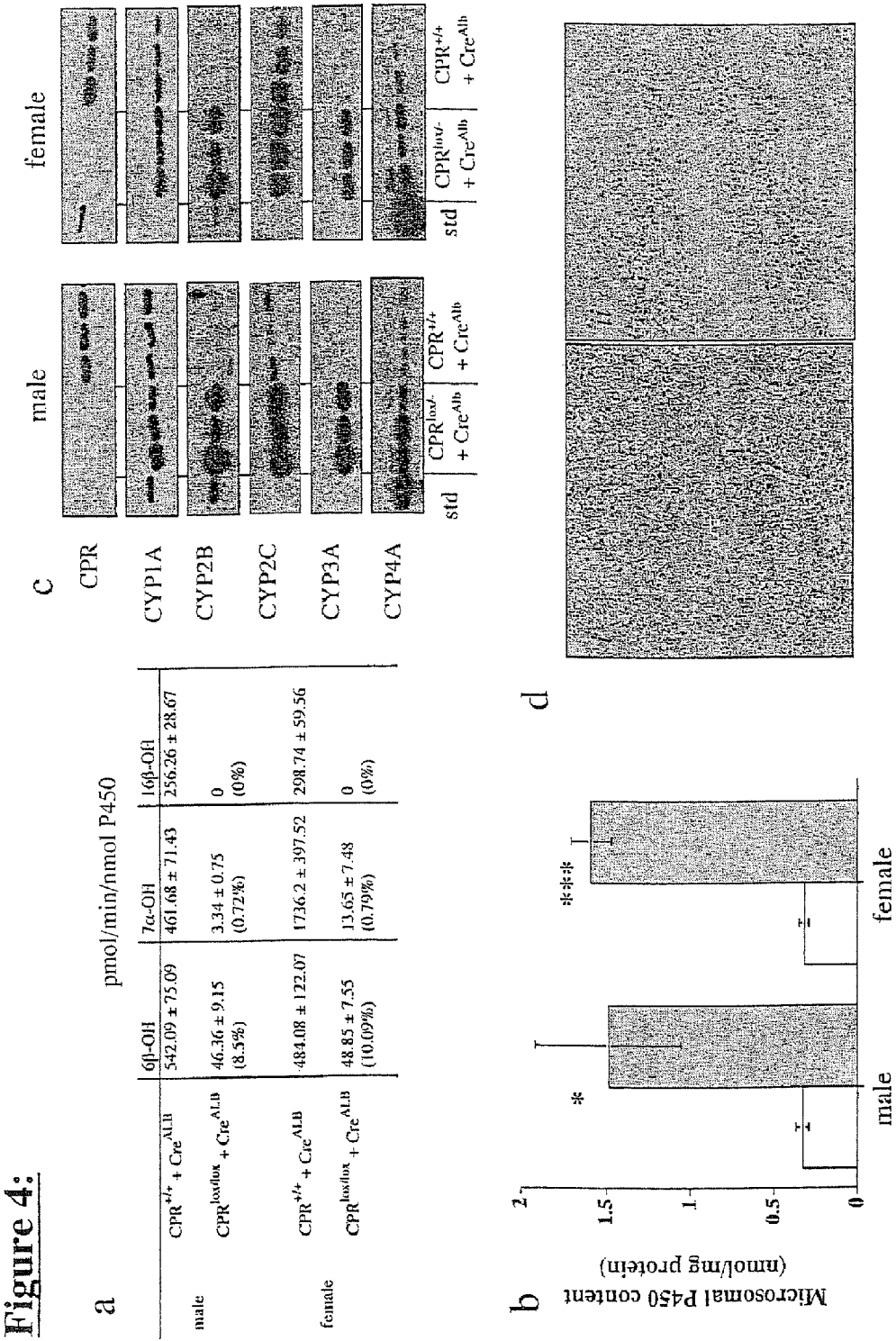
FIG. 4 illustrates CPR and P450 expression in hepatic CPR null mice.

FIG. 4: CPR and P450 Expression in Hepatic CPR Null Mice a Testosterone 6β, 7α and 16β hydroxylation in liver microsomes from CPR$^{+/+}$+CreALB and CPR$^{lox/lox}$+CreALB mice. Activities expressed in pmol/min/nmol P450, mean±SEM, figures in parentheses represent % activity in samples relative to wild-type=100%. Assay carried out in duplicate, n=4.

b Hepatic microsomal P450 content in adult male and female CPR$^{+/+}$+CreALB (white bars) and CPR$^{lox/lox}$+Cre-ALB (grey bars) mice (n=3). Values are expressed as mean±SEM. p<0.05 using an unpaired t-test.

c Immunoblotting of hepatic microsomes from adult male and female CPR$^{+/+}$+CreALB and CPR$^{lox/-}$+Cre$^{ALB}$ mice with polyclonal antisera to CPR and various P450s. std=protein standard.

d Immunostaining of liver sections from female CPR$^{lox/-}$+Cre$^{ALB}$ (i) and CPR$^{+/+}$+Cre$^{ALB}$ (ii) mice with polyclonal antisera to CYP3A1, phase contrast, magnification ×4.

FIG. 5: Drug Treatment of Hepatic CPR Null Mice a Hepatic glutathione and b serum alanine aminotransferase levels in adult male CPR$^{+/+}$+Cre$^{ALB}$ (closed squares) and CP$^{lox/-}$+Cre (open circles) mice following treatment with acetaminophen at 300 mg/kg i.p. at time zero (n=3). Values are expressed as mean±SEM.

c Time taken for regain of righting reflex in adult male mice of various genotypes following treatment with sodium pentobarbital at 20 mg/kg i.p. (n=3). Values are expressed as mean±SEM.

Methods

Generation of CPR Floxed and Knockout Mice

A replacement-type targeting vector was constructed from a 12 kb SalI fragment containing exons 3-16 of the mouse CPR gene. A cassette, flanked by same-orientation loxP sites and containing a selectable marker (neomycin (neo)), driven by the herpes simplex thymidine kinase (hsv-tk) promotor, was inserted into intron 4. A third loxP site was cloned into intron 15. The construct was transfected into GK129/1 embryonic (ES) cells by electroporation and the ES cells were subsequently plated out into 96 well plates and G418 selection applied. Eight G4185 resistant clones were found to have undergone specific homologous recombination as demonstrated by Southern analysis and two of these correctly targeted ES cell clones (CPR$^{lox/+}$) were expanded, injected into C57BL/6 blastocysts and transferred into 2.5 days post-coitum (dpc) recipient pseudopregnant mice. Male chimerae were bred to C57BL/6 mice and heterozygous offspring were screened by Southern analysis to confirm germline transmission of the CPR$^{lox/+}$ genotype. Five of these ES clones containing the CPR$^{lox}$ locus were transiently transfected with a vector containing the Cre recombinase gene (pMC1Cre). Colonies were obtained without selection and were isolated into a 96 well plate; after 3-4 days the plates were split into two duplicate plates, and after a further 3-4 days one plate was frozen and the other further split. G418 selection was applied for up to 5 days to one of these plates in order to identify sensitive colonies. DNA was prepared from the duplicate plate after 3-4 days later. ES clones (800) were tested by Southern blot analysis, using a 600 bp PCR fragment with primers 1105 and 1184 (FIG. 1a). Nine of those clones screened showed excision of the floxed sequence including exons 5 to 15. Two of these ES cell clones (CPR$^{+/-}$) were expanded and chimaeric mice generated. Male chimerae were bred to C57BL/6 mice and heterozygous offspring were screened by Southern blot analysis to confirm germline transmission.

Mouse Breeding and Maintenance

CPR$^{+/-}$ mice were maintained by random breeding with CPR$^{+/+}$ mice on a 129P2xC57BL/6 genetic background. CPR$^{+/-}$ mice were crossed with each other to determine the viability of a CPR$^{-/-}$ genotype.

CPR$^{lox/+}$ mice were crossed to produce homozygous CPR$^{lox/lox}$ mice and maintained by random breeding on a 129P2xC57BL/6 genetic background. The CPR$^{lox/lox}$ line was bred with CPR$^{+/-}$ to generate a CPR$^{lox/-}$ line.

A transgenic mouse line expressing Cre recombinase under control of the rat albumin promotor (4) was crossed onto both the CPR CPR$^{lox/lox}$ (CPR$^{lox/lox}$+Cre$^{ALB}$) and CPR$^{lox/-}$ (CPR$^{lox/-}$+Cre$^{ALB}$) lines to generate liver-specific CPR conditional knockout mice. The presence of the Cre$^{ALB}$ transgene was determined by PCR (data not shown).

Drug Treatment of Mice

Pentobarbital sleep time—adult male CPR$^{lox/lox}$+Cre$^{ALB}$, CPR$^{lox/-}$+Cre$^{ALB}$, CPR$^{lox/-}$ and CPR$^{+/+}$+Cre$^{ALB}$ mice (n=3) were given a single intraperitoneal (i.p.) dose of sodium pentobarbitone (Sagatal) at 20 mg/kg body weight. The time taken for the mice to lose, and subsequently to regain, their righting reflex was measured.

Acetaminophen treatment—adult male CPR$^{lox/-}$+Cre$^{ALB}$ and CPR$^{+/+}$+Cre$^{ALB}$ mice were administered acetaminophen intraperitoneally at 300 mg/kg body weight in phosphate-buffered saline (PBS). At various time-points after treatment, mice were sacrificed (n=4) and blood and tissues taken for analysis.

Immunoblotting and Biochemical Assays

Microsomal fractions were prepared from frozen tissues by differential centrifugation and protein concentration determined as previously described. Western blots were carried out as described previously using 9% sodium dodecylsulphate (SDS/PAGE) gels and electroblotted onto nitrocellulose membranes. A polyclonal antiserum raised against human CPR (5) was used as primary antibody, and a donkey anti-rabbit horseradish peroxidase IgG as secondary antibody (Scottish Antibody Production, Carluke, United Kingdom). Immunoreactivity was determined by chemiluminiscence (ECL Plus, Amersham-Pharmacia, Amersham, UK) and XAR5 autoradiographic film (Eastman Kodak). Glutathione levels were measured by the method of Sen et al. (6) and cytochrome P450 reductase activity was determined as previously described (5).

Blood Chemistry

Blood was collected by cardiac puncture into heparinised tubes, and serum prepared by centrifugation. Serum was either analysed immediately or stored at -70° C. for a period not exceeding 4 weeks. Analysis for serum alanine aminotransferase and cholesterol was carried out using commercially available kits (Infinity Reagents, Sigma, Poole, UK) on a Cobas Fara H centrifugal analyser (Roche, UK).

Histopathology

Tissue samples were either fixed in formalin-PBS for 24 h and transferred to 80% ethanol for storage, or snap-frozen embedded in OCT on cork discs and stored at −70° C. Formalin-fixed samples were sectioned and stained with haematoxylin and eosin, or processed for immunostaining with a polyclonal antibody against rat CPR or various P450s. Snap-frozen tissue samples were cryosectioned and processed for staining with Oil Red O to determine lipid content.

Statistical Analysis

Statistical analysis was carried out using the Statview program (v4.5) for Macintosh, Abacus Concepts, Berkeley, Calif.,

EXAMPLE 1

Generation of Conditional CPR Knockout Mice

CPR is a multi-domain protein containing NADPH/flavinadeninedinucleotide (FAD) and flavinmononucleotide (FMN) binding domains. When expressed in *E. coli*, these domains fold to form a functional polypeptide, which can, in the case of the FAD domain, independently catalyse the one electron reduction of a number of foreign compounds. For this reason, we made a construct, covering exons 3 to 16 of the CPR gene, where both of these domains would be deleted. (FIG. 1a). This construct was transfected into embryonic stem cells and a number of mouse lines generated. The correct integration of the floxed CPR targeting construct was confirmed by Southern analysis (FIG. 1b) of genomic DNA isolated from $CPR^{lox/+}$ mice (lanes 1 and 5 (9.2 kb/8 kb bands), while the pattern obtained from a wild-type mouse ($CPR^{+/+}$) is shown in lane 2 (8 kb band only). Genomic DNA of mice generated from ES cells in which Cre recombinase had been transiently expressed, resulted in deletion of the CPR gene between the first and third loxP sites. (FIG. 1b) lane 6 ($CPR^{+/-}$, 8 kb/3.2 kb bands). Mice homozygous for the floxed CPR locus ($CPR^{lox/lox}$) or with one floxed and one deleted CPR allele ($CPR^{lox/-}$) were generated by mating of appropriate mouse lines. Southern analysis of genomic DNA from these mice is shown in lanes 7 and 8 ($CPR^{lox/lox}$, 9.2 kb band only) and from in lanes 3 and 4 $CPR^{lox/-}$, 9.2 kb/3.2 kb). These latter mice were apparently completely normal, displaying no phenotypic differences from wild-type littermates: their growth and development, blood chemistry, organ size and structure, and fertility were identical (data not shown).

EXAMPLE 2

Generation of Hepatic CPR Null Mice

In order to test the ability of Cre recombinase to inactivate the CPR allele, mice carrying $CPR^{lox/-}$ were injected with a modified adenovirus in which Cre expression is regulated by the cytomegalovirus (CMV) promotor. One week after a single intravenous injection of AdCreI, hepatic CPR expression was reduced by >95% as measured by immunoblotting of hepatic microsomes and immunostaining of liver sections (not shown).

Specific hepatic deletion of CPR was achieved by crossing $CPR^{lox/lox}$ mice into a line where Cre expression was regulated by the rat albumin promotor. Mice identified as $CPR^{lox/+}+Cre^{ALB}$ were either backcrossed with $CPR^{lox/lox}$ mice to generate a $CPR^{lox/lox}+Cre^{ALB}$ line, or crossed with CPR heterozygous nulls to generate $CPR^{lox/-}+Cre^{ALB}$ mice. The presence of the $Cre^{ALB}$ transgene was determined by PCR (data not shown). Offspring born from either of these crosses were found in Mendelian proportions as predicted from parental genotype, indicating there was no embryonic lethality, from opportunistic expression of the Cre transgene during development.

$CPR^{lox/-}+Cre^{ALB}$ and $CPR^{lox/lox}+Cre^{ALB}$ mice displayed no overt phenotypic differences from their wild-type littermates in the postnatal period: mice of these genotypes grew and developed normally. As the albumin promotor becomes active neonatally, we investigated hepatic CPR levels in mice of 6-8 weeks of age. As mice were heterozygous for the CreALB genotype, three genotypes were anticipated, ie where no, one or both CPR alleles were deleted. This indeed proved to be the case. Deletion of floxed alleles appeared to occur with high efficiency; in mice where one CPR allele had been deleted, only half the expression and activity of CPR was found in both males and females (FIG. 2a, liver, tracks 2 & 3 vs. 4 & 5, and tracks 7 & 8 vs. 9 & 10). In mice of genotype $CPR^{lox/-}+Cre^{ALB}$, an immunoreactive CPR protein band was essentially absent in both males and females (FIG. 2a, lanes 1 and 6, respectively), indicating an almost complete lack of CPR protein in the microsomal fractions of the livers of these animals. Upon prolonged exposure (>10-fold normal) of the immunoblot shown in FIG. 2a, a very faint band corresponding to the correct molecular weight for CPR could be seen (not shown). Hepatic CPR activity in $CPR^{lox/-}+Cre$ mice was reduced by more than 90% in both males (92.5%) and females (94.5%) (FIG. 2b). The activity of cytochrome b5 reductase, an enzyme which could conceivably transfer electrons from NADH to the P450 system, was unchanged (not shown). In liver sections from CPR hepatic null mice stained with a polyclonal antiserum to CPR, only a very few cells contained immunoreactive protein (FIG. 2c), in contrast to the wild-type mice where CPR immunostaining was extensive across the entire section, tending to be more concentrated in the perivenous regions in a zonal fashion as previously reported. The deletion of CPR using a genetic strategy means that hepatocytes with no CPR immunostaining cannot have any CPR activity. The very low residual CPR activity observed in hepatic microsomal fractions may be due to continued expression of CPR in cells other than hepatocytes and/or in cells where the albumin promotor (and thus Cre expression) is inactive. The specificity of the CPR deletion was demonstrated by showing that no change was observed in CPR expression in the kidneys of $CPR^{lox/+}+Cre^{ALB}$, $CPR^{lox/+}$ and $CPR^{+/+}+Cre^{ALB}$ mice in both sexes (FIG. 2a, Kidney; lanes 3,4 & 5 (male) and 8, 9 & 10 (female)). A reduction in CPR protein level of approximately 50% was seen in $CPR^{lox/-}+Cre^{ALB}$ and in $CPR^{lox/-}$ mice was observed (FIG. 2a, lanes 1 & 2 (male) and 6 & 7 (female)) in offspring missing only one CPR allele. Again, protein expression reflected the CPR activity (FIG. 2b) in kidney microsomal fractions, with both male and female $CPR^{lox/-}+Cre^{ALB}$ mice exhibiting approximately half the CPR activity of $CPR^{+/+}+$Cre AL mice. Further confirmation of the tissue-specific nature of the CPR deletion was demonstrated by immunostaining kidney and lung sections from $CPR^{lox/-}+Cre^{ALB}$ and $CPR^{+/+}+Cre^{ALB}$ mice with CPR antiserum (FIG. 2c), where the staining was the same in both lines.

EXAMPLE 3

Characterisation of Hepatic CPR Null Mice

Mice nulled for hepatic CPR exhibited no overt phenotypic differences to controls. The mice grew at the same rate as their wild-type counterparts and there was no change in survival rates or behaviour. In spite of the known activity of the hepatic P450 monooxygenase system in the metabolism of androgens and oestrogens, CPR hepatic null mice exhibited normal fertility when mated to wild-type ($CPR^{+/+}$ or $CPR^{lox/lox}$) mice, indicating that hepatic hormone metabolism does not affect fertility.

More detailed analysis showed that both male and female hepatic CPR nulls displayed hepatomegaly, the liver being approximately 50% larger, in relation to body weight (7.5%), compared to wild-type mice (4%). Furthermore, the liver was pale in colour, and the tissue was mottled and friable (FIG. 3a,c). Microscopic examination revealed the presence of microvisicular and macrovisicular fatty changes, the former predominating (FIG. 3b, plates i and iv vs. iii and vii). Otherwise, hepatocytes in both the centrizonal and periportal regions appeared normal, with no apparent increase in hepatocyte proliferation or apoptosis.

The livers of mice lacking hepatic CPR were hyperlipidaemic, in terms of both cholesterol and triglycerides, as evidenced by staining with SRI9 (not shown) or Oil Red O (FIG. 3b, plates ii and vi vs. iv and viii). The increase in hepatic cholesterol was accompanied by the almost complete absence of bile acids in the gall bladder. This phenotypic observation could be explained by the inactivation of P450s such as CYP7A1 (cholesterol 7α-hydroxylase), reportedly the rate-limiting in bile acid biosynthesis. In the absence of cholesterol breakdown, we would have anticipated that an increase in circulating cholesterol would occur; however, exactly the opposite was observed, with serum cholesterol levels being reduced dramatically (>65%) (FIG. 3c). The control of cholesterol homeostasis is complex, however, and the above data demonstrate that the microsomal P450 system plays a key role in determining circulating cholesterol levels. A deletion of $CYP7A1^{-/-}$ has been described, which exhibited increased postnatal mortality but essentially unchanged serum cholesterol levels. The fact that increased mortality was not observed in this study was probably due to the conditional nature of the CPR deletion, occurring after the neonatal period, and reaching a peak after 3-4 weeks (not shown). It is interesting to note that the $CYP7A1^{-/-}$ mice were reported to have similar serum cholesterol levels to wild-type mice, and in order to assess the extent to which the accumulation of hepatic cholesterol in hepatic CPR null mice was due to de novo synthesis, these mice were placed on a fat-free diet for up to 3 months.

Under these conditions, the observed changes in hepatic and serum cholesterol were only partially reversed (not shown).

Under normal circumstances, cholesterol accumulation in the liver would trigger the feedback suppression of cholesterol uptake and biosynthesis by inhibiting the action of the sterol regulatory element binding protein (SREBP) transcription factors on a number of key lipogenic genes such as HMGCoA reductase, HMGCoA synthase and squalene synthase, and also the LDL receptor. It is interesting to note that transgenic mice expressing a truncated 'dominant positive' form of SREBP1 (7) displayed a similar hepatomegaly and elevation of hepatic lipid content as found here. However, these mice had essentially normal serum lipid chemistry.

The above data suggest that the P450 system plays additional important roles in regulating circulating cholesterol levels and that inhibition of these enzymes can reduce, rather than increase, cholesterol in the serum. Hepatic CPR nulls also demonstrated a marked increase in hepatic triglyceride levels, with a corresponding decrease in serum triglycerides (FIG. 3c). Although CYP4A proteins are involved in fatty acid metabolism, it is unlikely that the profound increase observed could be explained by the absence of this activity, indicating a potentially novel function of CPR and/or the P450 system in regulating lipid levels. No change in hepatic peroxisomal activity, often associated with CYP4A and fatty acid accumulation, was observed in hepatic CPR nulls (not shown). Counter intuitively, circulating triglyceride levels were reduced by 25% ($CPR^{lox/-}+Cre^{ALB}$) and 70% ($CPR^{lox/lox}+Cre^{ALB}$) in serum of reductase null mice relative to controls (FIG. 3c).

EXAMPLE 4

P450 Activity in Hepatic CPR Null Mice

In order to determine the effect of CPR deletion on hepatic P450 monoxygenase activities, we measured the microsomal hydroxylation of testosterone (FIG. 4a). When expressed as pmol metabolite per nmol P450, a 90% reduction in the formation of 6α-hydroxytestosterone, an activity associated with CYP3A proteins, was measured in both males and females, indicating that a lack of CPR in this tissue resulted in severely compromised P450 function. The 7phydroxylation of testosterone, carried out by P450s of the CYP2A subfamily, was decreased by >99% in both males and females, while 16p-hydroxylation was undetectable in hepatic CPR nulls of both sexes (FIG. 4a). In addition to the marked reduction in testosterone metabolism, the O-dealkylation of 7-methoxyresortifin was also almost completely ablated in $CPR^{lox/-}+Cre^{ALB}$ mice, being reduced by 99.5% in males and 98.5% in females, when expressed nmol metabolite per nmol P450 (not shown). It is thus clear that hepatic deletion of CPR results in the inactivation of multiple P450s in the liver.

Intriguingly, mice lacking hepatic CPR exhibited a profound increase in cytochrome P450 content; in males the increase was 450%, while in females it was greater than 500% (FIG. 4b).

This large increase in P450 expression was further demonstrated by immunoblotting of hepatic microsomes with antisera to P450s from different gene families (FIG. 4c). For certain of the enzymes, eg members of CYP2B and CYP3A gene families, the induction was extremely large. Indeed, these P450s were induced to at least as high a level as observed when potent exogenous P450 inducers are administered to mice. Hepatic immunostaining clearly showed that while expression of CYP3A P450s was confined to the perivenous or centrilobular area in wild-type mice, in null mice CYP3A was localised throughout the section at high levels (FIG. 4). These novel and fundamental observations demonstrate that endogenous factors, in addition to those identified as mediating the sexual differentiation of the murine P450 system can profoundly affect hepatic cytochrome P450 content. Why this occurs is however unclear. In the absence of P450 activity, endogenous inducing agents which are substrates for these enzymes, (e.g. glucocorticoids) may accumulate; alternatively, P450 turnover may be reduced. The rationale for this is based on the observation that CPR is the electron donor to haem oxygenase and increased CPR expression in transfected cells reduces P450 levels. Finally, there may be a novel compensatory regulatory response to the absence of P450 activity.

EXAMPLE 5

In Vivo Phenotypes

The analgesic drug paracetamol (acetaminophen) is activated by cytochrome P450s to a highly reactive hepatotoxic intermediate, N-acetylbenzoquinonimine (NAPQI), which can be detoxified by conjugation with glutathione; overwhelming this inactivation pathway results in hepatotoxicity, with fatal consequences. In order to unequivocally demonstrate the role of the P450 system in these effects, acetaminophen was administered as a single intraperitoneal dose to male control and hepatic CPR null mice (FIG. 5a, b). In controls, a 90% decrease in hepatic glutathione occurred within one hour of administration (FIG. 5a), whereas the level remained unchanged in CPR nulls. Furthermore, 24 h after treatment, wild-type mice showed a marked rise in serum ALT, indicative of extensive, probably fatal, liver damage, whereas in mice lacking hepatic CPR ALT remained unchanged.

Cytochrome P450s involved in drug metabolism are distributed throughout the tissues of the body; it has been estimated that a significant proportion of drug metabolism (up to 30%) may be extra-hepatic. In order to test the level of extra-hepatic metabolism as well as the in vivo effects of hepatic CPR nulls on drug disposition, we measured barbiturate-induced sleeping times. This method has been used since the 1960s as an indicator of drug metabolising activity. In controls, administration of pentobarbitone (20 mg/kg) failed to induce sleep; however, mice lacking hepatic CPR, of genotype $CPR^{3lox/-}+Cre^{ALB}$ or $CPR^{3lox/3lox}+Cre^{ALB}$, slept for a period in excess of 2 hours. Pentobarbitone treatment of CPR heterozygous null mice ($CPR^{+/-}$), ie lacking one CPR allele and therefore having approximately 50% less CPR activity, resulted in an average sleeping period of approximately 50 minutes, illustrating a clear gene-dosage effect, and also that CPR activity is rate-limiting in vivo for the metabolism of this substrate. The above profound changes in drug response show that extra-hepatic metabolism plays only a minor role in the disposition of this compound. The data also demonstrate that the potential alternate electron transport pathway for P450s, from NADH via cytochrome b5/b5 reductase, plays only a minimal role, if any, in drug disposition.

One of the most intriguing aspects of the animals of the present invention is that through the deletion of a single gene the functions of an entire multi-gene family has been ablated in a tissue-specific manner. In the case of the liver, the entire P450 system has essentially been inactivated, resulting in a profound reduction in bile acid production and drug metabolism. In spite of the hepatic phenotype, hepatic CPR null mice live (over 18 months) and reproduce normally. This extraordinary finding means that the hepatic P450 system in adults is not essential for life and furthermore accentuates its role in protecting mammals from toxic environmental agents. Currently, the hepatic metabolism of endogenous molecules such as steroid hormones does not appear to be of major significance in endogenous hormone homeostasis. However, the P450 system does play a major role in regulating lipid homeostasis and hepatic lipid levels. The animals of the present invention, tissues and/or cells derived therefrom, methods of their production and uses all as hereinbefore described here will allow fundamental questions, many of which have been unanswered for several decades, finally to be addressed.

That which is claimed is:

1. A method of assessing the effect of a drug, toxin or chemical, the method comprising exposing a conditional liver specific cytochrome P450 reductase (CPR) null homozygous transgenic mouse to a drug, toxin or chemical and comparing results of a selected parameter to results obtained from exposing a wild-type mouse to the same drug, toxin or chemical, wherein the selected parameter is selected from the group consisting of:
   (i) elimination rate of the drug, toxin or chemical or its metabolite(s);
   (ii) circulatory levels of the drug, toxin or chemical or its metabolite(s);
   (iii) disposition of the drug, toxin or chemical or its metabolite(s);
   (iv) drug, toxin or chemical bioavailability;
   (v) rate of metabolism of the drug, toxin or chemical;
   (vi) rate of clearance;
   (vii) extrahepatic contribution to metabolic rate and clearance of the drug, toxin or chemical or its metabolite(s);
   (viii) efficacy of the drug, toxin or chemical;
   (ix) toxicity of the drug, toxin or chemical; and
   (x) role of cytochrome P450 system in endogenous metabolism,
   and the comparison of the results provides information regarding the drug, toxin or chemical as it relates to the selected parameter,
   wherein the conditional liver specific cytochrome P450 reductase null homozygous transgenic mouse is produced by crossing a $CPR^{lox/lox}$ or $CPR^{lox/-}$ mouse with a $Cre^{ALB}$ mouse and wherein the null homozygous transgenic mouse has a phenotype of at least 90% reduction in hepatic CPR activity, at least 90% reduction in cytochrome P450 activity, and an increase in hepatic cytochrome P450 content by up to 500% as compared to a wild-type mouse.

2. A method of assessing a role of cytochrome P450s or cytochrome P450 reductase, the method comprising exposing a conditional liver specific cytochrome P450 reductase (CPR) null homozygous transgenic mouse to a product and comparing results of a selected parameter to results obtained from exposing a wild-type mouse to the same product, wherein the selected parameter is selected from the group consisting of:
   (i) elimination rate of the product or its metabolite(s);
   (ii) circulatory levels of the product or its metabolite(s);
   (iii) disposition of the product or its metabolite(s);
   (iv) product bioavailability;
   (v) rate of metabolism of the product;
   (vi) rate of clearance;
   (vii) extrahepatic contribution to metabolic rate and clearance of the product or its metabolite(s);
   (viii) efficacy of the product;
   (ix) toxicity of the product;
   (x) role of cytochrome P450 system in endogenous metabolism,
   (xi) pharmacological potency of agents subject to first pass metabolism;
   (xii) product distribution;
   (xiii) pharmacokinetics; and
   (xiv) rate-limiting step in drug/product disposition;
   and the comparison of the results provides information regarding the role of cytochrome P450s or cytochrome P450 reductase as it relates to the selected parameter,
   wherein the conditional liver specific cytochrome P450 reductase null homozygous transgenic mouse is produced by crossing a $CPR^{lox/lox}$ or $CPR^{lox/-}$ mouse with a $Cre^{ALB}$ mouse and wherein the null homozygous transgenic mouse has a phenotype of at least 90% reduction in hepatic CPR activity, and at least 90% reduction in cytochrome P450 activity, and an increase in hepatic cytochrome P450 content by up to 500% as compared to a wild-type mouse.

3. A method of screening for compounds useful for modulating cholesterol levels, comprising:
   (a) providing a conditional liver specific cytochrome P450 reductase null homozygous transgenic mouse with hepatic CPR activity reduced by more than 90%, wherein said mouse is produced by crossing a $CPR^{lox/lox}$ or $CPR^{lox/-}$ mouse with a $Cre^{ALB}$ mouse, and wherein said mouse has a phenotype of increased hepatic cholesterol and decreased circulating cholesterol,
   (b) administering a test compound to said transgenic mouse; and then (c) monitoring said transgenic mouse for altered levels of cholesterol as compared to a control mouse that has not been administered the test compound.

4. The method of claim 1, wherein said transgenic mouse is produced by introducing into a mouse embryonic stem cell a CPR targeting construct comprising exon 3-16 of the mouse CPR gene in a cassette flanked by the same orientation of loxP sites and comprising selectable marker neomycin (neo) operably linked to a herpes simplex virus thymidine kinase promoter (HSV-tk), selecting a mouse homozygous for a floxed CPR locus (CPR$^{lox/lox}$) and crossing the CPR$^{lox/lox}$ mouse with a Cre$^{ALB}$ line resulting in a homozygous liver specific CPR conditional knockout mouse.

5. A method of assessing at least one of the following activities selected from the group consisting of:
   (i) assessing a lead product selection based on in vivo metabolic parameters;
   (ii) crossing into drug discovery models so as to establish effect of metabolism on pharmacological activity and therapeutic outcome;
   (iii) determining the role of bile flow on product elimination; and
   (iv) studying drug/drug interactions due either to P450 or drug transporter effects, the method comprising exposing a conditional liver specific cytochrome P450 reductase (CPR) null homozygous transgenic mouse to a product, exposing a wild-type mouse to the same product, and comparing the metabolism and elimination of the product, wherein the comparison provides information regarding the product as it relates to said at least one activity and
   wherein the conditional liver specific cytochrome P450 reductase null homozygous transgenic mouse is produced by crossing a CPR$^{lox/lox}$ or CPR$^{lox/-}$ mouse with a Cre$^{ALB}$ mouse and wherein the null homozygous transgenic mouse has a phenotype of at least 90% reduction in hepatic CPR activity, at least 90% reduction in cytochrome P450 activity, an increase in hepatic cytochroine P450 content by up to 500% as compared to a wild-type mouse.

6. The method of claim 3, wherein said transgenic mouse is produced by introducing into a mouse embryonic stem cell a CPR targeting construct comprising exon 3-16 of the mouse CPR gene in a cassette flanked by the same orientation of loxP sites and comprising selectable marker neomycin (neo) operably linked to a herpes simplex virus thymidine kinase promoter (HSV-tk), selecting a mouse hornozygous for a foxed CPR locus (CPR$^{lox/lox}$) and crossing the CPR$^{lox/lox}$ mouse with a Cre$^{ALB}$ line resulting in a homozygous liver specific CPR conditional knockout mouse.

7. A method of assessing the role of bile acids in drug disposition, comprising:
   (a) providing a conditional liver specific cytochrome P450 reductase null homozygous transgenic mouse with hepatic CPR activity reduced by more than 90%, wherein said mouse is produced by crossing a CPR$^{lox/lox}$ or CPR$^{lox/-}$ mouse with a Cre$^{ALB}$ mouse, and wherein said mouse has a phenotype of an almost complete ablation of bile acid production,
   (b) administering a drug to said transgenic mouse; and
   (c) assessing the disposition of the drug.

8. The method of claim 7, wherein said transgenic mouse is produced by introducing into a mouse embryonic stem cell a CPR targeting construct comprising exon 3-16 of the mouse CPR gene in a cassette flanked by the same orientation of loxP sites and comprising selectable marker neomycin (neo) operably linked to a herpes simplex virus thymidine kinase promoter (HSV-tk), selecting a mouse homozygous for a floxed CPR locus (CPR$^{lox/lox}$) and crossing the CPR$^{lox/lox}$ mouse with a Cre$^{ALB}$ line resulting in a homozygous liver specific CPR conditional knockout mouse.

9. The method of claim 3, wherein the reduction in circulating cholesterol is greater than 65%.

10. The method of claim 1, wherein said transgenic mouse is produced by introducing into a mouse embryonic stem cell a CPR targeting construct comprising exon 3-16 of the mouse CPR gene in a cassette flanked by the same orientation of loxP sites and comprising selectable marker neomycin (neo) operably linked to a herpes simplex virus thymidine kinase promoter (HSV-tk), selecting a mouse homozygous for a floxed CPR locus (CPR$^{lox/lox}$) and crossing the CPR$^{lox/lox}$ mouse with a Cre$^{ALB}$ line resulting in a homozygous liver specific CPR conditional knockout mouse.

11. The method of claim 5, wherein said transgenic mouse is produced by introducing into a mouse embryonic stein cell a CPR targeting construct comprising exon 3-16 of the mouse CPR gene in a cassette flanked by the same orientation of loxP sites and comprising selectable marker neomycin (neo) operably linked to a herpes simplex virus thymidine kinase promoter (HSV-tk), selecting a mouse homozygous for a floxed CPR locus (CPR$^{lox/lox}$) and crossing the CPR$^{lox/lox}$ mouse with a Cre$^{ALB}$ line resulting in a homozygous liver specific CPR conditional knockout mouse.

\* \* \* \* \*

UNITED STATES PATENT AND TRADEMARK OFFICE
CERTIFICATE OF CORRECTION

PATENT NO. : 7,700,822 B2 Page 1 of 4
APPLICATION NO. : 10/306559
DATED : April 20, 2010
INVENTOR(S) : Wolf et al.

It is certified that error appears in the above-identified patent and that said Letters Patent is hereby corrected as shown below:

Column 21, Claim 1, Lines 52-67 and Column 22, Lines 1-19: Please replace the entire claim with the following language:

1. A method of assessing the effect of a drug, toxin or chemical; the method comprising:
   a) obtaining a transgenic mouse whose genome comprises a liver specific homozygous inactivation of the endogenous cytochrome P450 reductase (CPR) gene, wherein the mouse exhibits hyper lipidaemic liver, reduced bile acid in the gall bladder, at least 90% reduction in hepatic CPR activity and at least 90% reduction in cytochrome P450 activity, and an increase in hepatic cytochrome P450 content by up to 500% as compared to a wild-type mouse, wherein said liver specific cytochrome P450 reductase transgenic mouse is produced by crossing the mouse selected from the list consisting of mouse line having $CPR^{lox/lox}$ or a $CPR^{lox/-}$ genotype with a mouse from the $Cre^{ALB}$ line;
   (b) administering a drug, toxin or chemical to the transgenic mouse of step (a); (c) and comparing the results of selected parameters to results obtained from administering to a wild-type mouse the drug, toxin or chemical, wherein selected parameter is selected from a group consisting of:
   (i) elimination rate of the drug, toxin or chemical or its metabolite(s);
   (ii) circulatory levels of the drug, toxin or chemical or its metabolite(s);
   (iii) disposition of the drug, toxin or chemical or its metabolite(s);
   (iv) drug, toxin or chemical bioavailability;
   (v) rate of metabolism of the drug, toxin or chemical;
   (vi) rate of clearance;
   (vii) extrahepatic contribution to metabolic rate and clearance of the drug, toxin or chemical or its metabolite(s);
   (viii) toxicity of the drug, toxin or chemical;

Signed and Sealed this

Thirty-first Day of August, 2010

David J. Kappos
*Director of the United States Patent and Trademark Office*

CERTIFICATE OF CORRECTION (continued)
U.S. Pat. No. 7,700,822 B2 and wherein comparison of the results provides information regarding the drug, toxin or chemical as it relates to the selected parameter.

Column 22, Lines 20-56, Claim 2: Please replace entire claim with the following language:

2. A method of assessing a role of cytochrome P450s or cytochrome P450 reductase, the method comprising:
    a) obtaining a transgenic mouse whose genome comprises a liver specific homozygous inactivation of the endogenous cytochrome P450 reductase (CPR) gene, wherein the mouse exhibits hyper lipidaemic liver, reduced bile acid in the gall bladder, at least 90% reduction in hepatic CPR activity and at least 90% reduction in cytochrome P450 activity, and an increase in hepatic cytochrome P450 content by up to 500% as compared to a wild-type mouse, wherein said liver specific cytochrome P450 reductase transgenic mouse is produced by crossing the mouse selected from the list consisting of mouse line having $CPR^{lox/lox}$ or a $CPR^{lox/-}$ genotype with a from the $Cre^{ALB}$ line;
    (b) administering a product to the transgenic mouse of step (a) and then comparing the results of selected parameters to results obtained from administering to a wild-type mouse the product, wherein selected parameter is selected from a group consisting of:
        (i) elimination rate of the product or its metabolite(s);
        (ii) circulatory levels of the product or its metabolite(s);
        (iii) disposition of the product or its metabolite(s);
        (iv) product bioavailability;
        (v) rate of clearance;
        (vi) extrahepatic contribution to metabolic rate and clearance of the product or its metabolite(s);
        (vii) toxicity of the product;
        (viii) product distribution;
        (ix) pharmacokinetics;
        (x) rate-limiting step in production deposition; and
wherein comparison of the results provides information regarding the role of cytochrome P450s or cytochrome P450 reductase as it relates to the selected parameter.

CERTIFICATE OF CORRECTION (continued)
U.S. Pat. No. 7,700,822 B2

Column 22, Claim 3, Lines 57-67 and Column 23, Lines 1-3: Please replace the entire claim with the following language:

3. A method of screening for compounds useful for modulating cholesterol levels, comprising:
    (a) obtaining a transgenic mouse whose genome comprises a liver specific homozygous inactivation of the endogenous cytochrome P450 reductase (CPR) gene, wherein the mouse exhibits a phenotype of increased hepatic cholesterol and decreased circulating cholesterol, reduced bile acid in the gall bladder, at least 90% reduction in hepatic CPR activity and at least 90% reduction in cytochrome P450 activity, and an increase in hepatic cytochrome P450 content by up to 500% as compared to a wild-type mouse, wherein said liver specific cytochrome P450 reductase transgenic mouse is produced by crossing the mouse selected from the list consisting of mouse line having $CPR^{lox/lox}$ of a $CPR^{lox/-}$ genotype with a from the $Cre^{ALB}$ line;
    (b) administering a test compound to said transgenic mouse; and
    (c) monitoring said transgenic mouse for altered levels of cholesterol as compared to a control mouse that has not been administered the test compound.

Column 23, Claim 5, Lines 4-40: Please replace the entire claim with the following language:

5. A method of assessing at least one of the following activities selected from the group consisting of: (i) assessing lead product selection based on in vivo metabolic parameters; (ii) determining the role of bile flow on product elimination; and (iii) studying drug/drug interactions due either to P450 or drug transporter effects, the method comprising: (a) obtaining a transgenic mouse whose genome comprises a liver specific homozygous inactivation of the endogenous cytochrome P450 reductase (CPR) gene, wherein the mouse exhibits hyper lipidaemic liver, reduced bile acid in the gall bladder, at least 90% reduction in hepatic CPR activity and at least 90% reduction in cytochrome P450 activity, and an increase in hepatic cytochrome P450 content by up to 500% as compared to a wild-type mouse, wherein said liver specific cytochrome P450 reductase transgenic mouse is produced by crossing the mouse selected from the list consisting of mouse line having $CPR^{lox/lox}$ or a $CPR^{lox/-}$ genotype with a from the $Cre^{ALB}$ line;
    (b) administering a produce to the transgenic mouse of step (a); and
    (c) comparing the metabolism and elimination of the product, wherein the comparison provides information regarding the product as it relates to said at least one activity.

Column 23, Claim 6, Line 47: Please correct "hornozygous" to read -- homozygous --; and correct "foxed" to read -- floxed --

CERTIFICATE OF CORRECTION (continued)
U.S. Pat. No. 7,700,822 B2

Column 24, Claim 7, Lines 4-14: Please replace the entire claim with the following language:

7. A method of assessing the role of bile acids in drug disposition, comprising:
        (a) obtaining a transgenic mouse whose genome comprises a liver specific homozygous inactivation of the endogenous cytochrome P450 reductase (CPR) gene, wherein the mouse exhibits hyper lipidaemic liver, reduced bile acid production, at least 90% reduction in hepatic CPR activity and at least 90% reduction in cytochrome P450 activity, and an increase in hepatic cytochrome P450 content by up to 500% as compared to a wild-type mouse, wherein said liver specific cytochrome P450 reductase transgenic mouse is produced by crossing the mouse selected from the list consisting of mouse line having $CPR^{lox/lox}$ or a $CPR^{lox/-}$ genotype with a from the $Cre^{ALB}$ line;
        (b) administering a drug to the transgenic mouse of step (a); and
        (c) assessing the disposition of the drug.

Column 24, Claim 10, Line 27: Please correct "claim 1" to read -- claim 2 --

Claim 11, Line 38: Please correct "embryonic stein cell" to read -- embryonic stem cell --